(12) United States Patent  (10) Patent No.: US 8,161,831 B2
Fukuma  (45) Date of Patent: Apr. 24, 2012

(54) ANALYZER, SAMPLE TRANSPORTATION METHOD FOR ANALYZER, AND COMPUTER PROGRAM PRODUCT

(75) Inventor: Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 440 days.

(21) Appl. No.: 12/399,498

(22) Filed: Mar. 6, 2009

(65) Prior Publication Data

US 2009/0223308 A1  Sep. 10, 2009

(30) Foreign Application Priority Data

Mar. 7, 2008 (JP) ................................ 2008-058007

(51) Int. Cl.
*B01L 3/02* (2006.01)
(52) U.S. Cl. .................................................... 73/864.21
(58) Field of Classification Search ........................ None
See application file for complete search history.

(56) References Cited

U.S. PATENT DOCUMENTS

| 5,623,415 | A | * | 4/1997 | O'Bryan et al. | 700/225 |
| 6,117,392 | A | * | 9/2000 | Hanawa et al. | 422/65 |
| 6,290,907 | B1 | * | 9/2001 | Takahashi et al. | 422/65 |
| 7,264,111 | B2 | | 9/2007 | Veiner | |
| 7,283,217 | B2 | | 10/2007 | Ikeuchi et al. | |
| 2005/0281707 | A1 | * | 12/2005 | Nakaya et al. | 422/63 |
| 2007/0110617 | A1 | | 5/2007 | Nagai et al. | |

FOREIGN PATENT DOCUMENTS

JP  9-43248 A  2/1997
JP  11-295321 A  10/1999

* cited by examiner

*Primary Examiner* — Hezron E Williams
*Assistant Examiner* — Mark A Shabman
(74) *Attorney, Agent, or Firm* — Brinks Hofer Gilson & Lione

(57) ABSTRACT

An analyzer comprising: a first measurement unit; a second measurement unit; a transportation device for transporting samples to at least one measurement unit selected from the first measurement unit and the second measurement unit; and a transportation controller for determining whether or not a sample is transportable to the selected one measurement unit on the basis of at least one of a state notification of the first measurement unit and a state notification of the second measurement unit, wherein the transportation controller controls the transportation device to perform a sample transportation operation of transporting the sample to the selected one measurement unit when the sample is transportable to the selected one measurement unit, and to perform the other transportation operation than the sample transportation operation when the sample is not transportable to the selected one measurement unit, is disclosed. Sample transportation method and a computer program product are also disclosed.

10 Claims, 18 Drawing Sheets

FIG. 15

EVENT LIST

| |
|---|
| RACK INPUT COMPLETION |
| RACK OUTPUT COMPLETION |
| TEST TUBE PRESENCE CHECK COMPLETION |
| SAMPLE ID/MEASUREMENT ORDER ASSIGNMENT COMPLETION |
| TEST TUBE INSERTION COMPLETION TO FIRST MEASUREMENT UNIT |
| TEST TUBE INSERTION COMPLETION TO SECOND MEASUREMENT UNIT |
| TEST TUBE EXTRACTION COMPLETION FROM FIRST MEASUREMENT UNIT |
| TEST TUBE EXTRACTION COMPLETION FROM SECOND MEASUREMENT UNIT |
| TEST TUBE EXTRACTION REQUEST |
| MEASUREMENT UNIT STATE NOTIFICATION |
| NEXT SAMPLE SUCTION READY NOTIFICATION |

FIG. 16

PRIORITY OF COMMAND

HIGH PRIORITY ↑

| 1 | OUTPUT RACK |
|---|---|
| 2 | INPUT RACK |
| 3 | EXTRACT TEST TUBE FROM FIRST MEASUREMENT UNIT |
| 4 | EXTRACT TEST TUBE FROM SECOND MEASUREMENT UNIT |
| 5 | INSERT TEST TUBE TO FIRST MEASUREMENT UNIT |
| 6 | INSERT TEST TUBE TO SECOND MEASUREMENT UNIT |
| 7 | CHECK WHETHER OR NOT THERE IS TEST TUBE |
| 8 | ASSIGN SAMPLE ID/MEASUREMENT ORDER |

LOW PRIORITY

OPERATION AT THE TIME OF PRIOR SAMPLE MEASUREMENT (FIRST EMBODIMENT)

ANALYZER, SAMPLE TRANSPORTATION METHOD FOR ANALYZER, AND COMPUTER PROGRAM PRODUCT

RELATED APPLICATIONS

This application claims priority under 35 U.S.C. §119 to Japanese Patent Application No. JP2008-058007 filed Mar. 7, 2008, the entire content of which is hereby incorporated by reference.

FIELD OF THE INVENTION

The present invention relates to an analyzer, a sample transportation method for an analyzer, and a computer program product, and more particularly, to an analyzer provided with a plurality of measurement units and a sample transportation method using a plurality of measurement units.

BACKGROUND OF THE INVENTION

Analyzers and transportation systems automatically transporting samples to a plurality of measurement units have been known. In addition, a transportation system capable of promptly performing of a process of samples has been known (see Japanese Patent Application Laid-Open No. 9-43248).

The transportation system described in Japanese Patent Application Laid-Open No. 9-43248 is provided with a start stock unit holding a plurality of racks housing a plurality of samples before processing, and is configured to select a predetermined rack from the start stock unit on the basis of information of measurement items for the samples and a load (burden) state of each measurement unit and to input the selected predetermined rack to a transportation line. With such a configuration, it is possible to efficiently transport the samples to each measurement unit, and thus it is possible to promptly process the samples.

However, in the transportation system described in Japanese Patent Application Laid-Open No. 9-43248, after the selected predetermined rack is input to the transportation line, for example, when an interruption cause of measurement occurs such as error or measurement instruction of a prior sample (urgent sample) in the measurement unit at a transportation destination, the process of the samples in the transported predetermined rack is interrupted. That is, in the transportation system described in Japanese Patent Application Laid-Open No. 9-43248, it is difficult to promptly cope with the occurrence of the interruption cause of the measurement in the measurement unit. As a result, there is a problem that the process of the sample cannot be promptly performed.

SUMMARY OF THE INVENTION

The scope of the present invention is defined solely by the appended claims, and is not affected to any degree by the statements within this summary.

A first aspect of the present invention is an analyzer comprising: a first measurement unit; a second measurement unit; a transportation device for transporting samples to at least one measurement unit selected from the first measurement unit and the second measurement unit; and a transportation controller for determining whether or not a sample is transportable to the selected one measurement unit on the basis of at least one of a state notification of the first measurement unit and a state notification of the second measurement unit, wherein the transportation controller controls the transportation device to perform a sample transportation operation of transporting the sample to the selected one measurement unit when the sample is transportable to the selected one measurement unit, and to perform the other transportation operation than the sample transportation operation when the sample is not transportable to the selected one measurement unit.

A second aspect of the present invention is a sample transportation method for an analyzer, the method comprising: determining whether or not a sample is transportable to selected one measurement unit on the basis of at least one of a state notification of a first measurement unit and a state notification of a second measurement unit; performing a sample transportation operation of transporting the sample to the selected one measurement unit when the sample is transportable to the selected one measurement unit; and performing the other transportation operation than the sample transportation operation when the sample is not transportable to the selected one measurement unit.

A third aspect of the present invention is a computer program product for controlling transportation of samples on an analyzer comprising a first measurement unit, a second measurement unit, and a transportation device configured to transport the samples to the first measurement unit and the second measurement unit, the computer program product comprising: a computer readable medium; and instructions, on the computer readable medium, adapted to enable a general purpose computer to perform operations comprising: determining whether or not a sample is transportable to selected one measurement unit on the basis of at least one of a state notification of the first measurement unit and a state notification of the second measurement unit; performing a sample transportation operation of transporting the sample to the selected one measurement unit when the sample is transportable to the selected one measurement unit; and performing the other transportation operation than the sample transportation operation when the sample is not transportable to the selected one measurement unit.

BRIEF DESCRIPTION OF THE DRAWINGS

FIG. 15 is a diagram illustrating event notification of the blood analyzer according to the embodiment shown in FIG. 1.

FIG. 16 is a diagram illustrating priority of commands of the blood analyzer according to the embodiment shown in FIG. 1.

DETAILED DESCRIPTION OF THE PREFERRED EMBODIMENTS

The preferred embodiments of the present invention will be described hereinafter with reference to the drawings.

Figure 1:
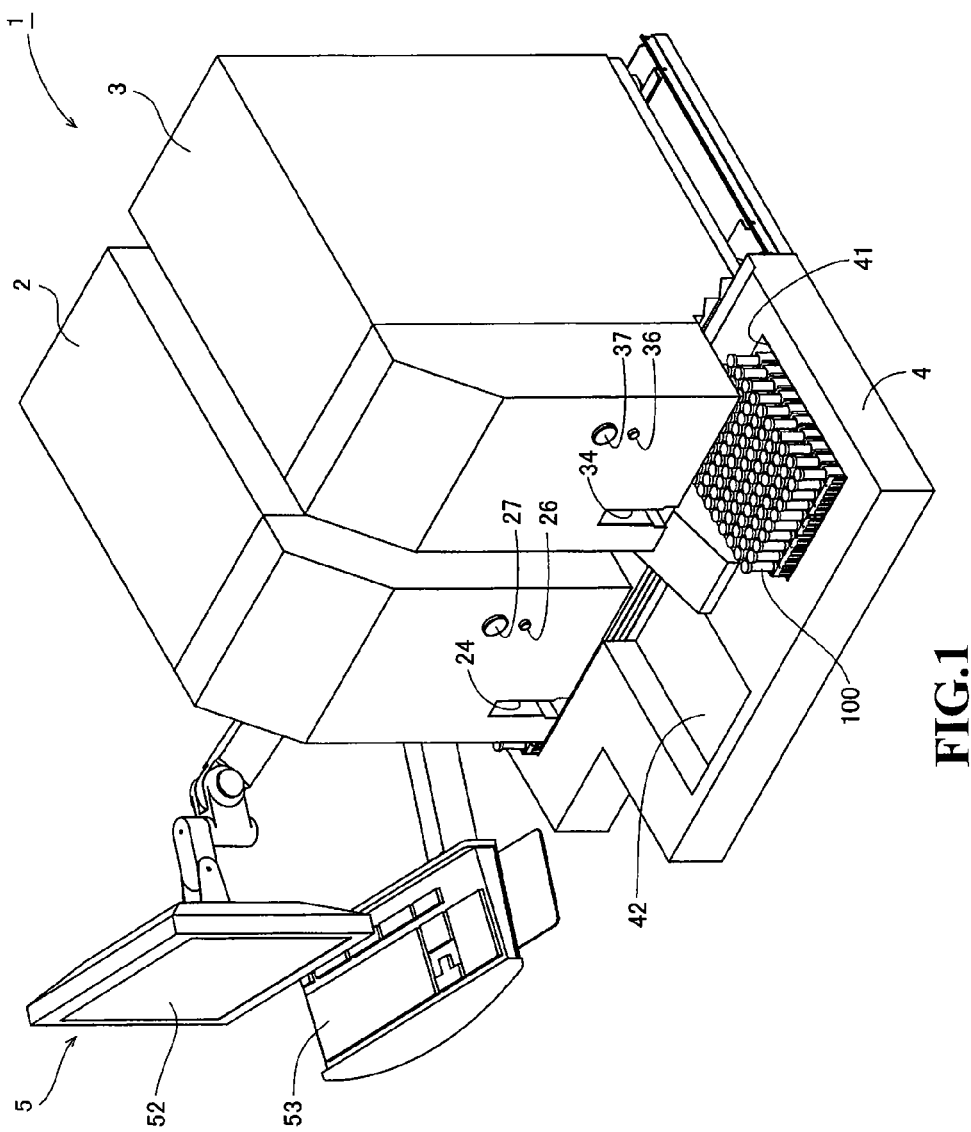
FIG. 1 is a perspective view illustrating an overall configuration of a blood analyzer according to an embodiment of the invention.

FIG. 1 is a perspective view illustrating an overall configuration of a blood analyzer according to an embodiment of the invention. FIG. 2 to FIG. 10 are views for explaining detailed sections of the blood analyzer according to an embodiment shown in FIG. 1. First, the overall configuration of the blood analyzer 1 according to the embodiment of the invention will be described with reference to FIG. 1 to FIG. 10. In the embodiment, the invention is applied to a blood analyzer that is an example of an analyzer.

Figure 2:
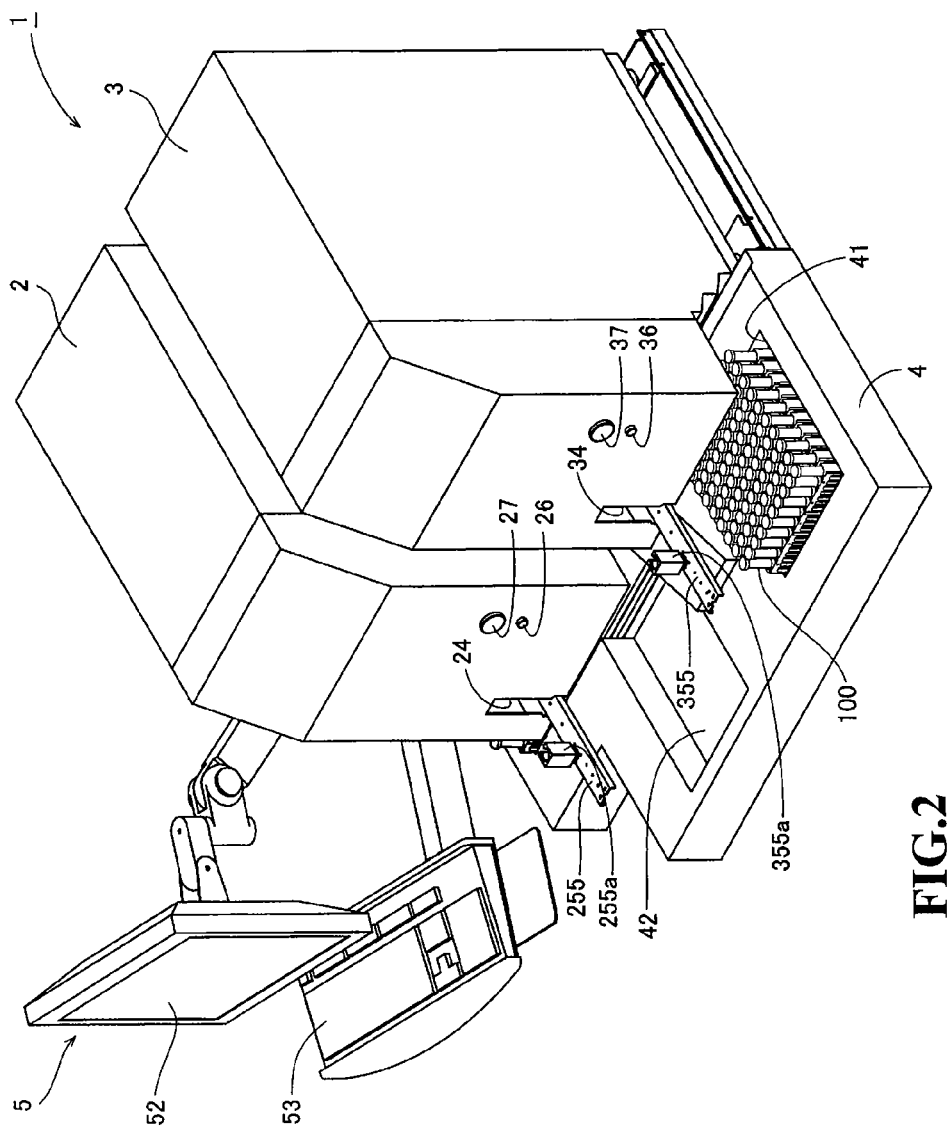
FIG. 2 is a perspective view for explaining detailed sections of the blood analyzer according to the embodiment shown in FIG. 1.

As shown in FIG. 1 and FIG. 2, the blood analyzer 1 according to an embodiment of the invention is provided with two measurement units of a first measurement unit 2 and a second measurement unit 3, a sample transportation device (sampler) 4 disposed on the front side of the first measurement unit 2 and the second measurement unit 3, and a control device 5 including a PC (personal computer) electrically connected to the first measurement unit 2, the second measurement unit 3, and the sample transportation device 4. The blood analyzer 1 is connected to a host computer 6 (see FIG. 3) by the control device 5.

The blood analyzer 1 is not a transportation system in which a plurality of analyzers are connected by the known transportation device but a standalone analyzer. In addition, the blood analyzer 1 may be mounted on the transportation system.

Figure 3:
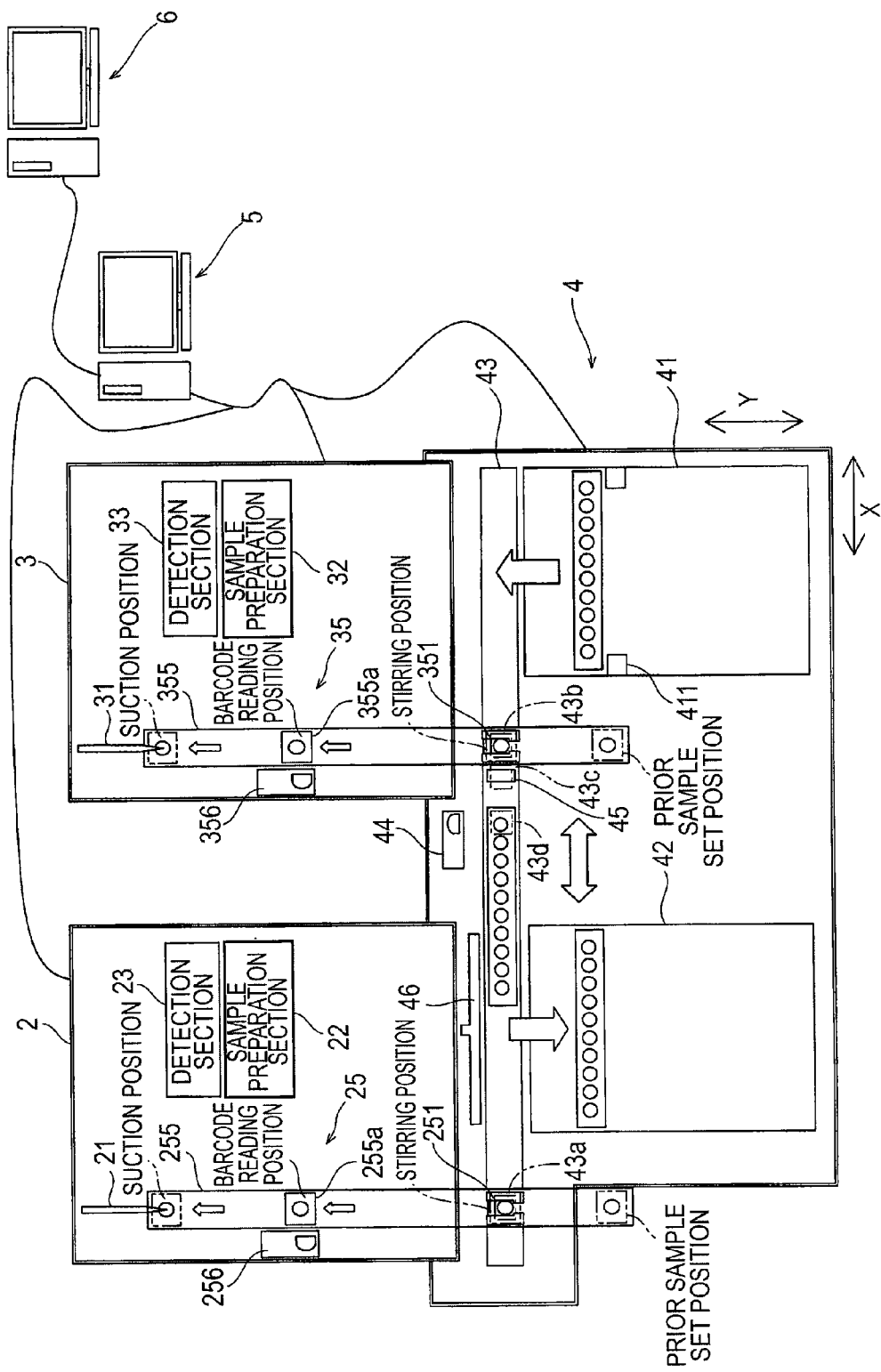
FIG. 3 is a schematic diagram illustrating a measurement unit and a sample transportation device of the blood analyzer according to the embodiment shown in FIG. 1.

As shown in FIG. 1 to FIG. 4, the first measurement unit 2 and the second measurement unit 3 are substantially the same type of measurement units (In the embodiment, the second measurement unit 3 uses the same measurement principle as the first measurement unit 2, and measures samples with respect to the same measurement items. The second measurement unit 3 also measures measurement items which are not analyzed by the first measurement unit 2), and are disposed adjacent to each other. Herein, the same type includes a case in which a plurality of measurement items of the first measurement unit 2 and a plurality of measurement items of the second measurement unit 3 are partially common, as well as a case in which two measurement units measure samples with respect to the completely same measurement items. As shown in FIG. 3, the first measurement unit 2 and the second measurement unit 3 include sample suction sections 21 and 31 for sucking blood as a sample from a sample container (test tube) 100, sample preparation sections 22 and 32 for preparing detection samples from the blood sucked by the sample suction sections 21 and 31, and detection sections 23 and 33 for detecting blood cells from the detection samples prepared by the sample preparation sections 22 and 32, respectively. The first measurement unit 2 and the second measurement unit 3 further include insertion holes 24 and 34 (see FIG. 1 and FIG. 2) for inserting a sample container 100 accommodated in a rack 101 (see FIG. 5) transported by the sample transportation device 4, and sample container transportation sections 25 and 35 for inserting the sample container 100 from the rack 101 therein and transporting the sample container 100 to a suction position (see FIG. 3) of the sample suction sections 21 and 31, respectively. As shown in FIG. 1 and FIG. 2, sample set section open and close buttons 26 and 36 and prior sample measurement start buttons 27 and 37 are provided on the outer surface of the first measurement unit 2 and the second measurement unit 3, respectively. As shown in FIG. 3, the first measurement unit 2 and the second measurement unit 3 are provided with state notification units 28 and 38 for transmitting state notifications to a control device 5, respectively.

Needles (not shown) are provided at the front end portions of the sample suction sections 21 and 31, respectively. The sample suction sections 21 and 31 are configured to move in the vertical direction (direction indicated by the arrow Z), respectively. The sample suction sections 21 and 31 are configured to pass through an airtight cap of the sample container 100 transported to the suction position by moving downward and to suck inner blood.

The detection sections 23 and 33 are configured to perform RBC detection (detection of red blood cell) and PLT detection (detection of platelet) by a sheath flow DC detection method and to perform HGB detection (detection of hemoglobin in blood) by an SLS-hemoglobin method. The detection sections 23 and 33 are configured to perform WBC detection (detection of white blood cell) by a flow cytometry method using semiconductor laser.

The detection result obtained by the detection sections 23 and 33 are transmitted to the control device 5, as measurement data (measurement result) of samples. The measurement data is a basis of a final analysis result (the number of red blood cells, the number of platelets, the amount of hemoglobin, the number of white blood cells, etc.) provided for a user.

Figure 4:
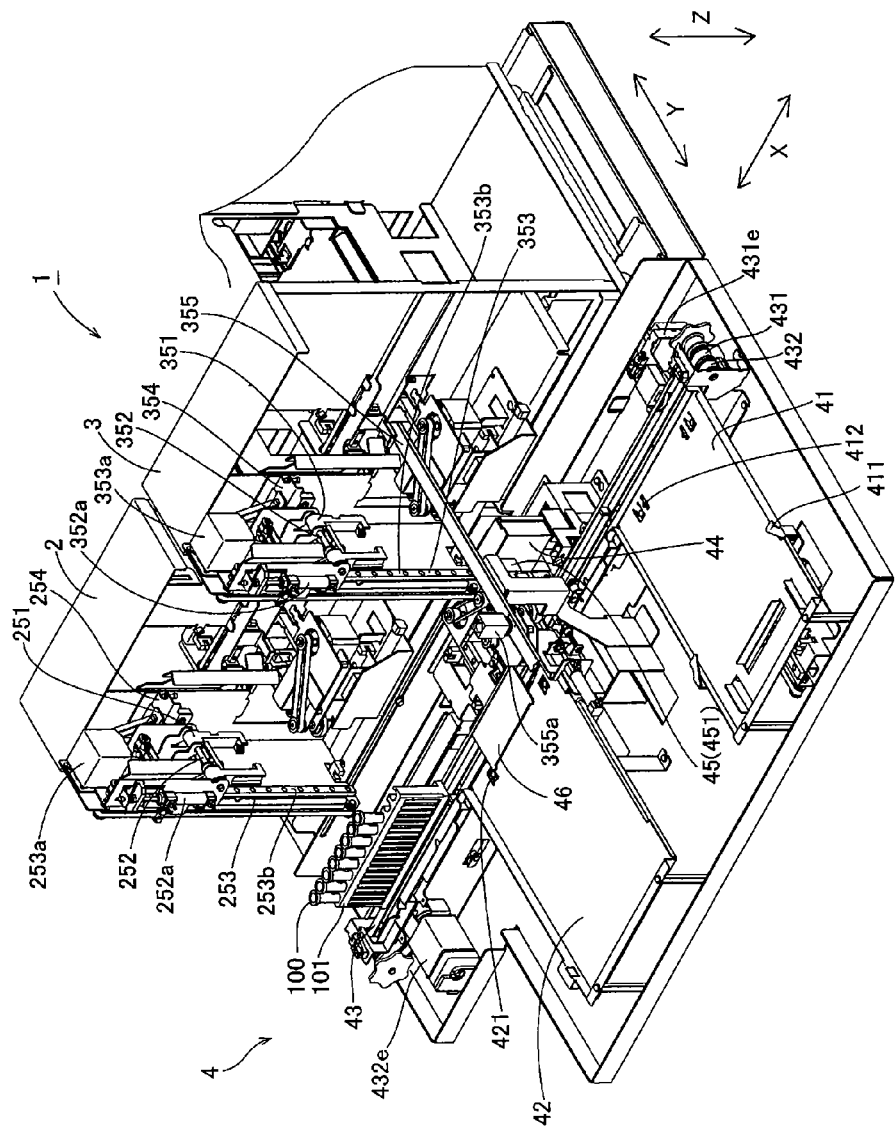
FIG. 4 is a perspective view illustrating a measurement unit and a sample transportation device of the blood analyzer according to the embodiment shown in FIG. 1.

As shown in FIG. 3 and FIG. 4, the sample container transportation sections 25 and 35 has hand sections 251 and 351 for gripping the sample container 100, opening and closing sections 252 and 352 for opening and closing the hand sections 251 and 351 to grip the sample container 100, vertical moving sections 253 and 353 for straightly moving the hand sections 251 and 351 in the vertical direction (direction indicated by the arrow Z), and stirring sections 254 and 354 for moving the hand sections 251 and 351 in a pendulum shape in the vertical direction (direction indicated by the arrow Z), respectively. The sample container transportation sections 25 and 35 further have sample container moving sections 255 (see FIG. 3) and 355 for holding the sample container 100 acquired from the rack 101 by the hand sections 251 and 351 to sample set sections 255a (see FIG. 3) and 355a, and for horizontally and straightly moving in the direction indicated by the arrow Y to the suction position of the sample suction sections 21 and 31, and barcode reading sections 256 and 356, respectively.

The hand sections 251 and 351 are disposed above a transportation path of the rack 101 transported by the sample transportation device 4, respectively. The hand sections 251 and 351 are configured so that when the sample container 100 is transported to a first providing position 43a for providing samples at the first measurement unit 2 and a second providing position 43b (see FIG. 3) for providing samples at the second measurement unit 3, the hand sections 251 and 351 move downward (direction indicated by the arrow Z) to grip the sample container 100 accommodated in the rack 101 by opening and closing the opening and closing sections 252 and 352, respectively. The hand sections 251 and 351 are configured to move the gripped sample container 100 upward to be extracted from the rack 101, and then to move in a pendulum shape by the stirring sections 254 and 354 (e.g., 10 times reciprocation), respectively. Accordingly, it is possible to stir blood in the gripped sample container 100 by the hand sections 251 and 351. After completion of stirring, the hand sections 251 and 351 are configured to move downward and then open the gripping of the sample container 100 by the opening and closing sections 252 and 352. Accordingly, it is possible to set the sample container 100 at the sample set sections 255a and 355a of the sample container moving sections 255 and 355 by the hand sections 251 and 351.

The opening and closing sections 252 and 352 are configured to open and close the hand sections 251 and 351 to grip the sample container 100 by power of air cylinders 252a and 352a, respectively.

The vertical moving sections 253 and 353 are configured to move the hand sections 251 and 351 in the vertical direction (direction indicated by the arrow Z) along rails 253b and 353b by power of stepping motors 253a and 353a, respectively.

The stirring sections 254 and 354 are configured to move the hand sections 251 and 351 in a pendulum shape in the vertical direction (direction indicated by the arrow Z) by power of stepping motors (not shown), respectively.

The sample container moving sections 255 and 355 are configured to horizontally move the sample set sections 255a and 355a in the direction indicated by the arrow Y by power of stepping motors (not shown), respectively. Accordingly, as shown in FIG. 3, the sample container moving sections 255 and 355 can transport the sample container 100 set at the sample set sections 255a and 355a to a prior sample set position, a stirring position, a barcode reading position, and a suction position. The sample container moving sections 255 and 355 are configured to pass through the upside of the transportation path of the rack 101 and transport the sample container 100, so as to intersect the transportation path of the rack 101 transported in the direction indicated by the arrow X in the plan view. The sample set sections 255a and 355a are configured to move to a prior sample set position (see FIG. 3) when a user presses down the sample set section open and close buttons 26 and 36 (see FIG. 1 and FIG. 2). The sample container moving sections 255 and 355 are configured to clamp (fix) the sample container 100 at each suction position by a restriction section (not shown).

Figure 5:
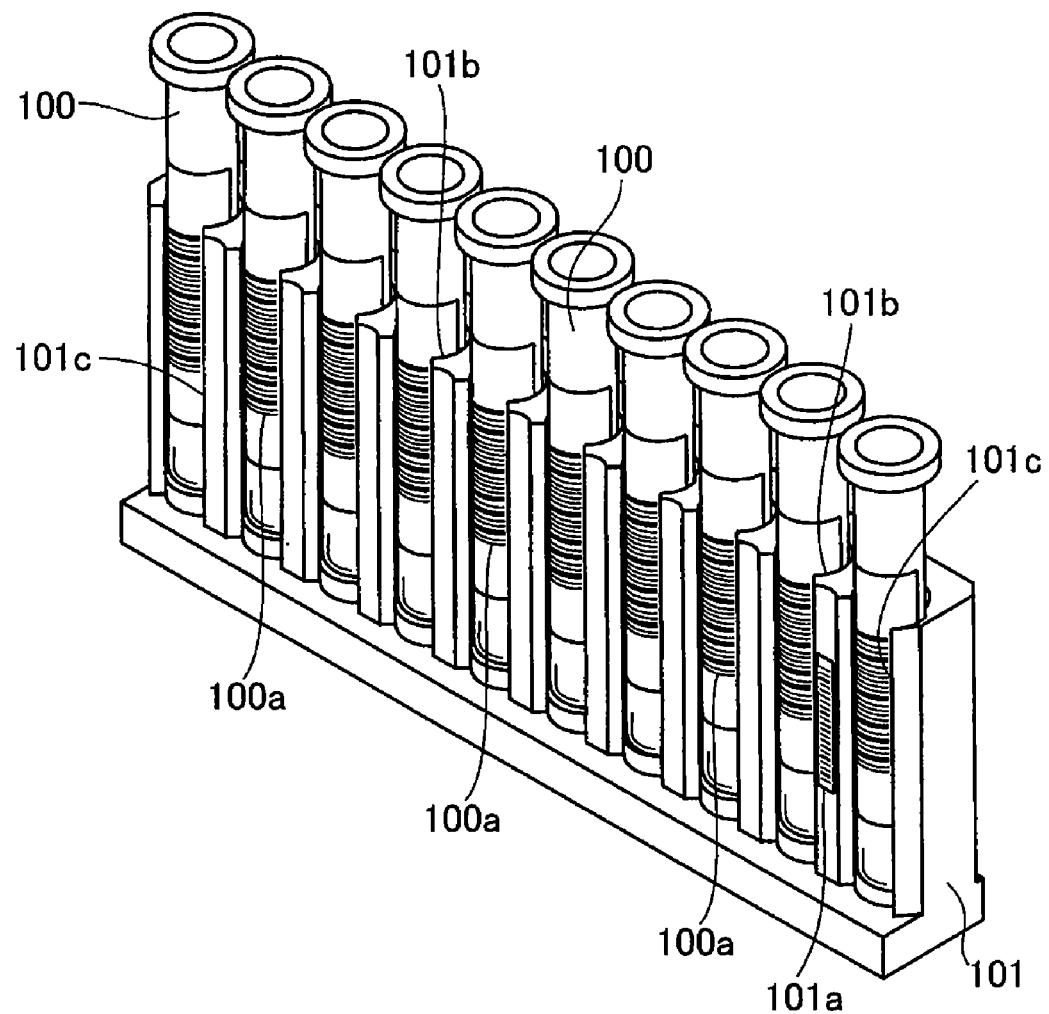
FIG. 5 is a perspective view illustrating a rack and sample containers of the blood analyzer according to the embodiment shown in FIG. 1.

The barcode reading sections 256 and 356 are configured to read a barcode 100a attached to each sample container 100 as shown in FIG. 5. The barcode reading sections 256 and 356 are configured to read the barcode 100a of the sample container 100 while rotating in the horizontal direction with the sample container 100 as a target held to the sample set sections 255a and 355a by a rotation device (not shown). Accordingly, even when the barcode 100a of the sample container 100 is attached to the opposite side to the barcode reading sections 256 and 356, it is possible to turn the barcode 100a toward the barcode reading sections 256 and 356 by rotating the sample container 100. Each barcode 100a of each sample container 100 is uniquely attached to each sample, and is used to manage the analysis result of each sample.

The sample set section open and close buttons 26 and 36 are configured to be pressed down by a user at the time of measuring a prior sample.

The prior sample measurement start buttons 27 and 37 are configured to be pressed down by a user. When the user sets a prior sample at the sample set sections 255a and 355a and then presses down the prior sample measurement start buttons 27 and 37, the sample set sections 255a and 355a at which the prior sample is set are inserted into the measurement unit and the measurement is started.

Figure 6:
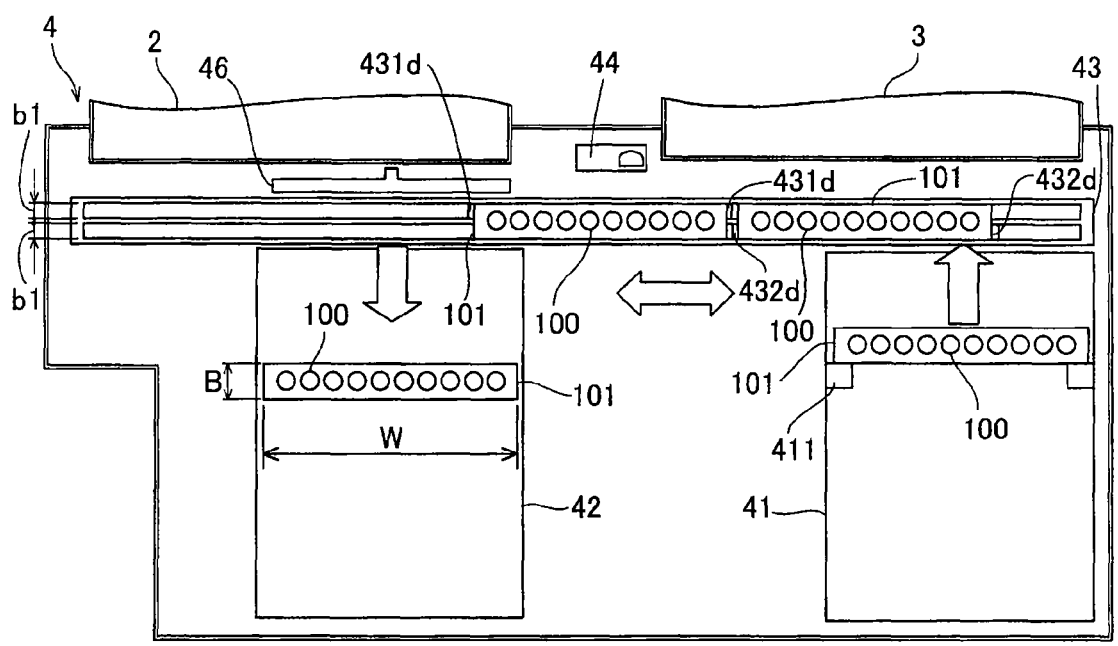
FIG. 6 is a plan view for explaining the sample transportation device of the blood analyzer according to the embodiment shown in FIG. 1.

As shown in FIG. 4 and FIG. 6, the sample transportation device 4 includes a before-analysis rack holding section 41 capable of holding the plurality of racks 101 accommodating the sample containers 100 for accommodating samples before performing analysis, an after-analysis rack holding section 42 capable of holding the plurality of racks 101 accommodating the sample containers 100 for accommodating the samples after performing analysis, a rack transportation section 43 for horizontally and straightly moving the rack 101 in the direction indicated by the arrow X, a barcode reading section 44, a presence sensing sensor 45 (see FIG. 4) for sensing whether or not there is the sample container 100, and a rack output section 46 for moving the rack 101 into the after-analysis rack holding section 42.

The before-analysis rack holding section 41 having a rack input section 411 is configured to output the rack 101 held to the before-analysis rack holding section 41 one by one onto the rack transportation section 43 by moving the rack input section 411 in the direction indicated by the arrow Y. The rack input section 411 is configured to be driven by a stepping motor (not shown) provided below the before-analysis rack holding section 41. The before-analysis rack holding section 41 having a restriction section 412 (see FIG. 4) in the vicinity of the rack transportation section 43 is configured to restrict movement of the rack 101 so that the rack 101 output onto the rack transportation section 43 once does not return into the before-analysis rack holding section 41.

The after-analysis rack holding section 42 having a restriction section 421 (FIG. 4) in the vicinity of the rack transportation section 43 is configured to restrict movement of the rack 101 so that the rack 101 moved into the after-analysis rack holding section 42 once does not return to the rack transportation section 43.

In the embodiment, as shown in FIG. 3, the rack transportation section 43 is configured to transport the rack 101 so that the samples are transported to the first providing position 43a for providing samples at the first measurement units 2 and the second providing position 43b for providing samples at the second measurement unit 3. When the samples are transported to the providing position 43a or 43b, the hand section 251 or 351 of the corresponding measurement unit grips the sample container 100 of the transported samples. The rack transportation section 43 is configured to wait until finishing the operation of extracting the sample container 100 from the rack 101. Accordingly, the sample container 100 is taken out of the rack 101 by the hand section 251 or 351 in a state where the sample container 100 accommodating the samples remains stationary at the sample providing position 43a or 43b. Therefore, it is possible to securely take the sample container 100 out of the rack 101 by the hand section 251 or 351. The rack transportation section 43 is configured to transport the rack 101 so as to transport the samples to a sample presence check position 43c for checking whether or not there is the sample container 100 for accommodating the samples by the presence sensing sensor 45 and a reading position 43d for reading the barcode 100a of the sample container 100 for accommodating the samples by the barcode reading section 44.

Figure 7:
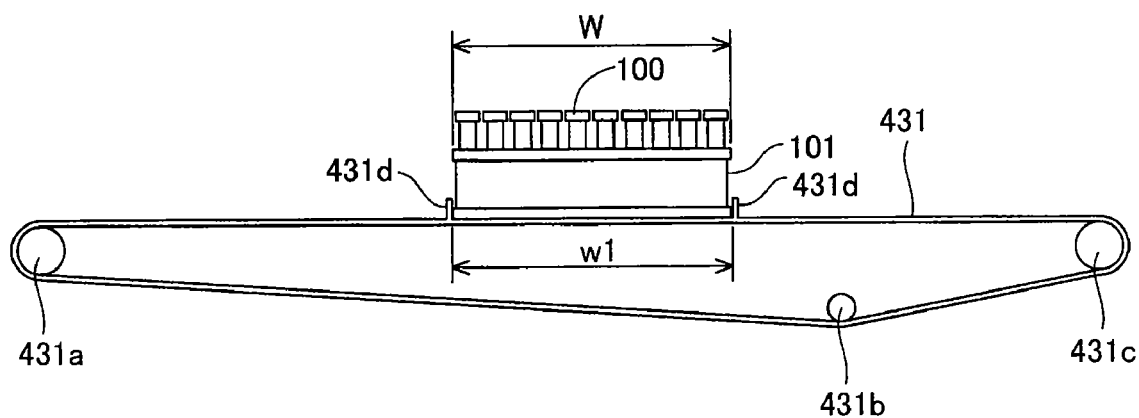
FIG. 7 is a side view for explaining the sample transportation device of the blood analyzer according to the embodiment shown in FIG. 1.
Figure 8:
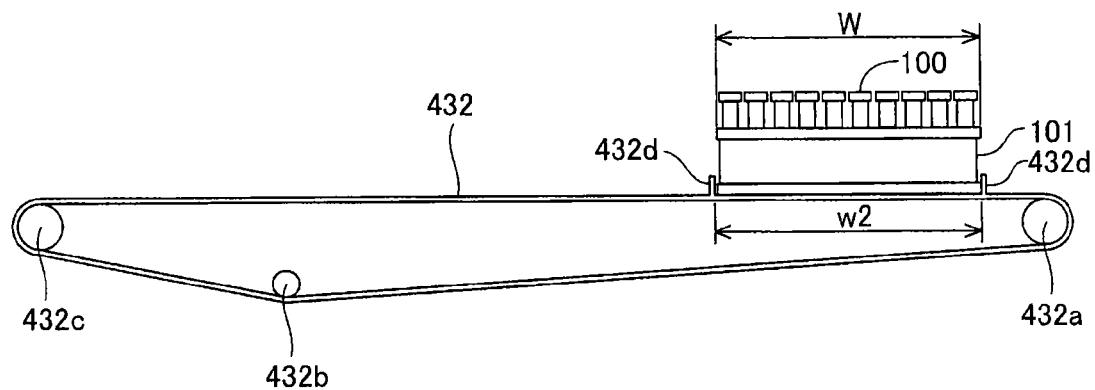
FIG. 8 is a side view for explaining the sample transportation device of the blood analyzer according to the embodiment shown in FIG. 1.

The rack transportation section 43 has two belts of a first belt 431 and a second belt 432 capable of moving independently from each other. Widths b1 and b2 (see FIG. 6) of the first belt 431 and the second belt 432 in the direction indicated by the arrow Y are a half of a width B of the rack 101 in the direction indicated by the arrow Y or smaller. Accordingly, the first belt 431 and the second belt 432 are disposed in parallel so as not to protrude from the width B of the rack 101 when the rack transportation section 43 transports the rack 101. As shown in FIG. 7 and FIG. 8, the first belt 431 and the second belt 432 have a ring shape, and are disposed to surround rollers 431a to 431c and rollers 432a to 432c, respectively. Each two protrusion pieces 431d and 432d are formed at outer peripheral sections of the first belt 431 and the second belt 432 to have an inner width w1 (see FIG. 7) and w2 (see FIG. 8) slightly (e.g., about 1 mm) larger than the width W of the rack 101 in the direction indicated by the arrow X. The first belt 431 is configured to move the rack 101 in the direction indicated by the arrow X by moving along outer peripheries of the rollers 431a to 431c by a stepping motor 431e (see FIG. 4), with the rack 101 held in the protrusion piece 431d. The second belt 432 is configured to move the rack 101 in the direction indicated by the arrow X by moving along outer peripheries of the rollers 432a to 432c by a stepping motor 432e (see FIG. 4), with the rack 101 held in the protrusion piece 432d. The first belt 431 and the second belt 432 are configured to move the rack 101 independently from each other.

The barcode reading section 44 is configured to read the barcode 100a of the sample container 100 shown in FIG. 5 and to read the barcode 101a attached to the rack 101. The barcode reading section 44 is configured to read the barcode 100a of the sample container 100 while rotating in the horizontal direction with the sample container 100 as a target accommodated in the rack 101 by a rotation device (not shown). Accordingly, even when the barcode 100a of the sample container 100 is attached to the opposite side to the barcode reading section 44, it is possible to turn the barcode 100a toward the barcode reading section 44 by rotating the sample container 100. The barcode 101a of the rack 101 is uniquely attached to each rack, and is used to manage the analysis result of each sample.

The presence sensing sensor 45 is a contact type sensor, and has a contact piece 451 (see FIG. 4) having a curtain shape, a light emitting element (not shown) emitting light, and a light receiving element (not shown). The presence sensing sensor 45 is configured so that the contact piece 451 is bent when the contact piece 451 comes into contact with a sensing object that is a sensing target, and thus light emitted from the light emitting element is reflected to the contact piece 451, and the reflected light enters the light receiving element. Accordingly, when the sample container 100 that is a sensing target accommodated in the rack 101 passes through the downside of the presence sensing sensor 45, the contact piece 451 is bent by the sample container 100, thereby sensing that there is the sample container 100.

The rack output section 46 is opposed to the after-analysis rack holding section 42 with the rack transportation section 43 interposed therebetween, and is configured to horizontally and straightly move in the direction indicated by the arrow Y. Accordingly, when the rack 101 is transported to a position (hereinafter, referred to as a rack output position) between the after-analysis rack holding section 42 and the rack output section 46, the rack output section 46 is moved to the after-analysis rack holding section 42, thereby pressing the rack 101. Therefore, it is possible for the rack 101 to move into the after-analysis rack holding section 42.

Figure 9:
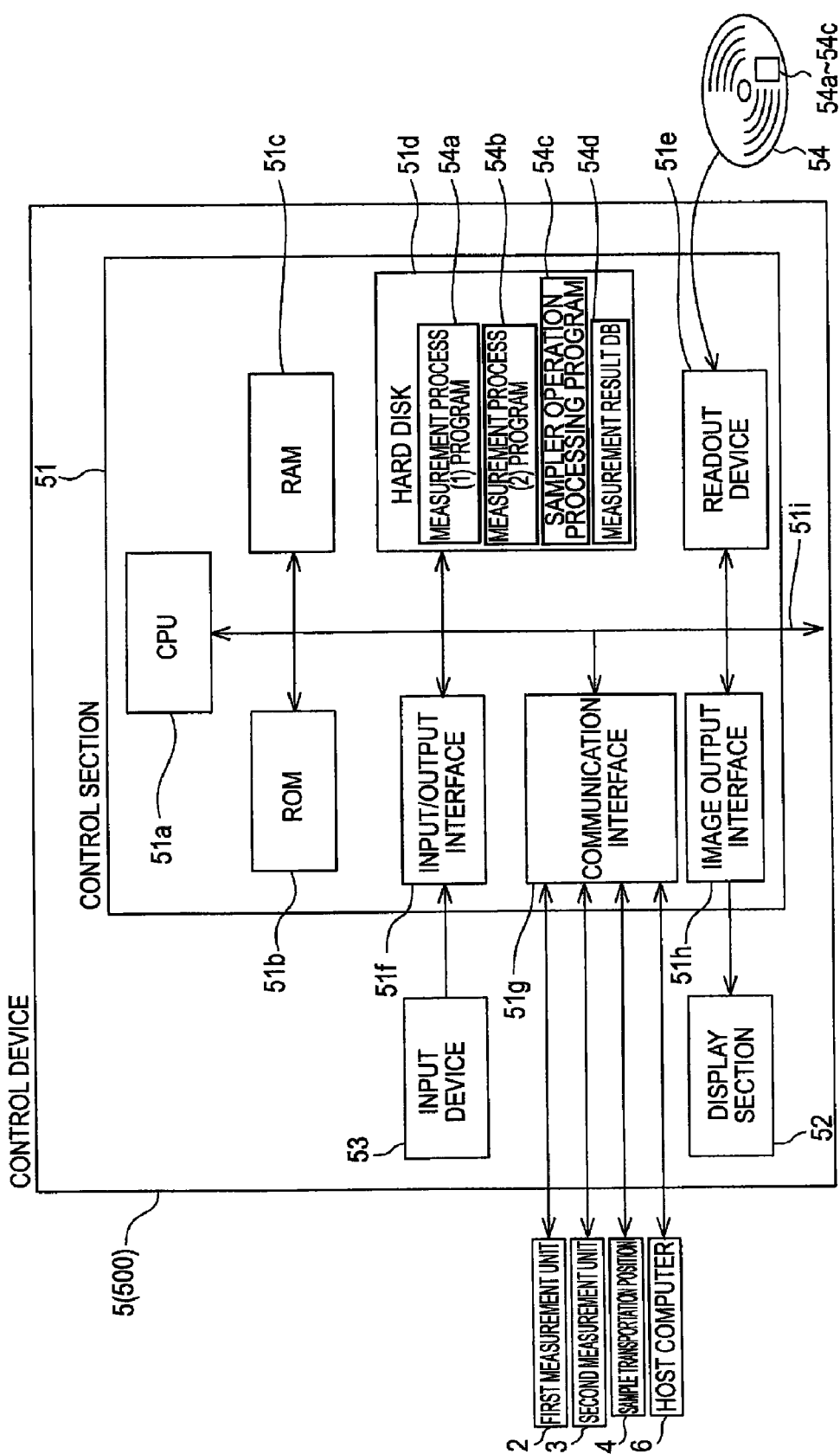
FIG. 9 is a block diagram for explaining a control device of the blood analyzer according to the embodiment shown in FIG. 1.
Figure 10:
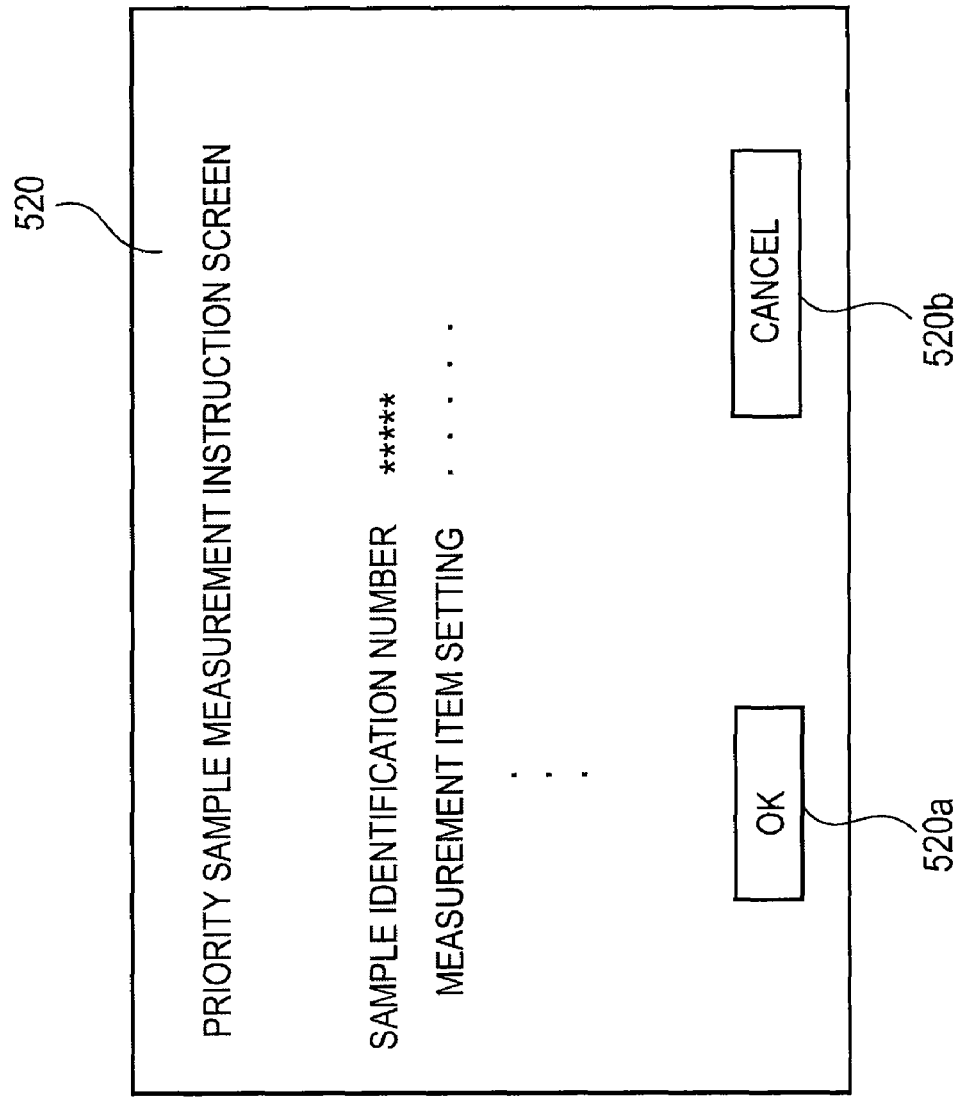
FIG. 10 is a diagram illustrating a prior sample measurement instruction screen of the blood analyzer according to the embodiment shown in FIG. 1.

As shown in FIG. 1, FIG. 2, and FIG. 9, the control device 5 is configured of a personal computer (PC) or the like, and includes a control unit 51 configured of a CPU, a ROM, a RAM, and the like, a display unit 52, and an input device 53. The display unit 52 is provided to display analysis results and the like obtained by analyzing data of digital signals transmitted from the first measurement unit 2 and the second measurement unit 3. The display unit 52 is configured to input sample identification numbers for identifying samples by a user or to display a prior sample measurement instruction screen 520 (see FIG. 10) for setting measurement items and the like, in the measurement of a prior sample needing to be measured prior to the other samples.

Next, a configuration of the control device 5 will be described. As shown in FIG. 9, the control device 5 is configured of a computer 500 mainly including a control unit 51, a display unit 52, and an input device 53. The control unit 51 mainly includes a CPU 51a, a ROM 51b, a RAM 51c, a hard disk 51d, a readout device 51e, an input/output interface 51f, a communication interface 51g, and an image output interface 51h. The CPU 51a, the ROM 51b, the RAM 51c, the hard disk 51d, the readout device 51e, the input/output interface 51f, the communication interface 51g, and the image output interface 51h are connected by a bus 51i.

The CPU 51a can execute a computer program stored in the ROM 51b and a computer program loaded on the RAM 51c. The CPU 51a executes application programs 54a to 54c, whereby the computer 500 functions as the control device 5.

The ROM 51b is configured of a mask ROM, a PROM, an EPROM, an EEPROM, or the like, in which computer programs executed by the CPU 51a and data used for the computer programs are recorded.

The RAM 51c is configured of an SRAM, a DRAM, or the like. The RAM 51c is used to read the computer programs recorded in the ROM 51b and the hard disk 51d. The RAM 51c is used as a work area of the CPU 51a when the computer programs are executed.

In the hard disk 51d, various computer programs such as an operating system and application programs executed by the CPU 51a, and data used for executing the computer programs are installed. A measurement processing program 54a for the first measurement unit 2, a measurement processing program 54b for the second measurement unit 3, and a measurement processing program 54c for the sample transportation device 4 are also installed in the hard disk 51d. The application programs 54a to 54c are executed by the CPU 51a, thereby controlling an operation of each section of the first measurement unit 2, the second measurement unit 3, and the sample transportation device 4. A measurement result database 54d is also installed therein.

The readout device 51e is configured of a flexible disk drive, a CD-ROM drive, a DVD-ROM drive, or the like, and can read computer programs or data recorded in a transportable recording medium 54. The application programs 54a to 54c are stored in the transportable recording medium 54, the computer 500 reads the application programs 54a to 54c from the transportable recording medium 54, and the application programs 54a to 54c can be installed in the hard disk 51d.

The application programs 54a to 54c are not only provided by the transportable recording medium 54 but may be provided from an external device connected to communicate with the computer 500 by an electric communication line (irrespective of wire and wireless) through the electric communication line. For example, the application programs 54a to 54c are stored in a hard disk of a server computer on the Internet, the computer 500 accesses to the server computer, the application programs 54a to 54c are downloaded, and the application programs 54a to 54c are installed in the hard disk 51d.

An operating system providing graphical user interface environment such as Windows (trade mark) produced by Microsoft Inc. in USA is installed in the hard disk 51d. In the following description, it is assumed that the application programs 54a to 54c are operated on the operating system.

The input/output interface 51f is configured of, for example, a serial interface such as USB, IEEE1394, and RS-232C, a parallel interface such as SCSI, IDE, and IEEE1284, an analog interface including a D/A converter and A/D converter, and the like. The input device 53 is connected to the input/output interface 51f, and a user uses the input device 53, thereby inputting data to the computer 500.

The communication interface 51g is, for example, an Ethernet (trade mark) interface. The computer 500 can transmit and receive data among the first measurement unit 2, the second measurement unit 3, the sample transportation device 4, and the host computer 6 using a predetermined communication protocol by the communication interface 51g.

The image output interface 51h is connected to the display unit 52 configured of LCD, CRT, or the like, and displays video signals based on the image data given from the CPU 51a on the display unit 52. The display unit 52 displays images (screen) according to the input video signals.

With such a configuration, the control unit 51 is configured to analyze components of an analysis target using the measurement result transmitted from the first measurement unit 2 and the second measurement unit 3, and to acquire the analysis result (the number of red blood cells, the number of platelets, the amount of hemoglobin, the number of white blood cells, etc.).

As shown in FIG. 5, ten container accommodating sections 101b are formed in the rack 101 to accommodate ten sample containers 100 in series. The container accommodating sections 101b are provided with opening sections 101c so that the barcode 100a of each accommodated sample container 100 is visible.

Figure 11:
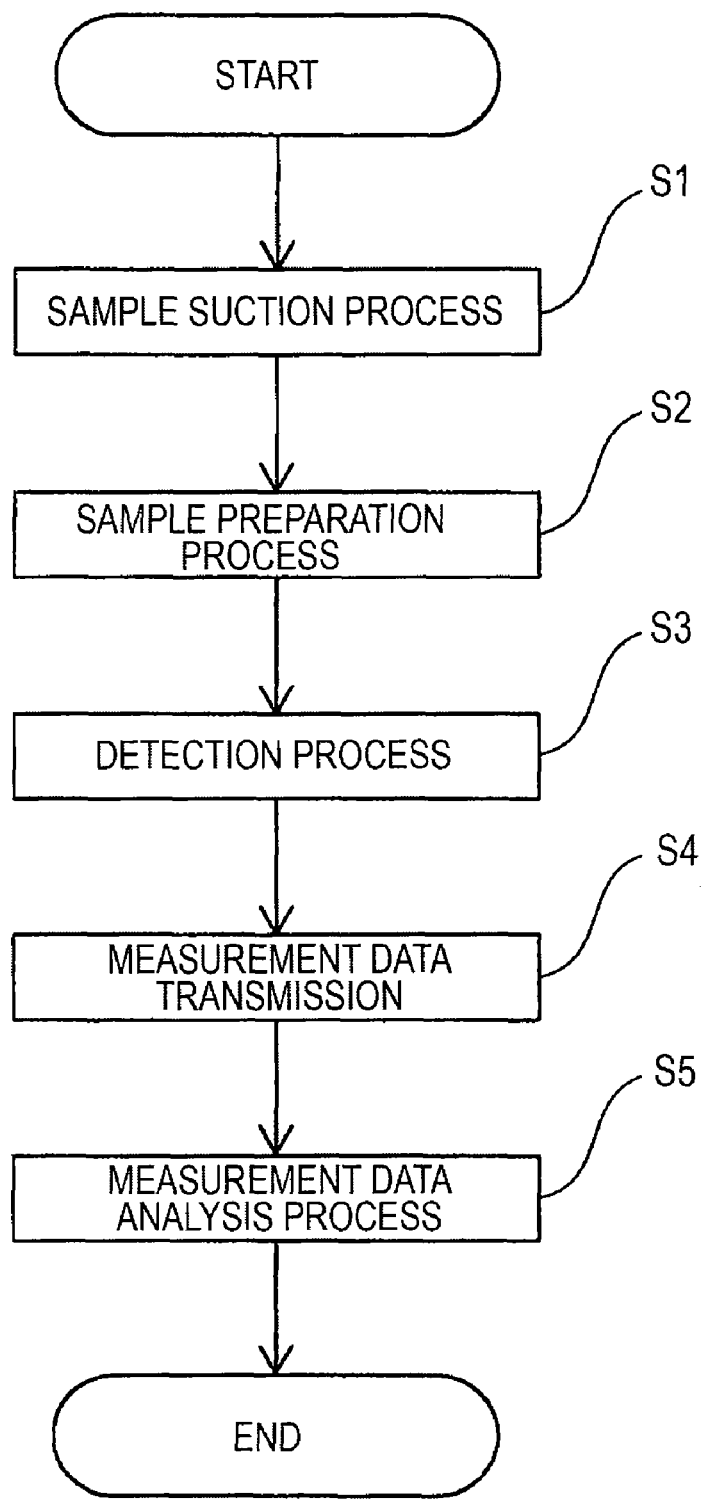
FIG. 11 is a flowchart for explaining a measurement processing operation performed by a measurement processing program of the blood analyzer according to the embodiment shown in FIG. 1.

FIG. 11 is a flowchart for explaining measurement processing operations by the measurement processing programs of the blood analyzer according to the embodiment shown in FIG. 1. Next, the measurement processing operations by the measurement processing programs 54a and 54b of the blood analyzer 1 according to the embodiment will be described with reference to FIG. 11. The components of the analysis target are measured in the first measurement unit 2 and the second measurement unit 3 in the same manner. Accordingly, the case where the components of the analysis target are measured by the first measurement unit 2 will be described herein as a representative example.

First, in Step S1, suction of samples is performed from the transported sample container 100 to the suction position (see FIG. 3) by the sample suction section 21. In Step S2, a detection sample is prepared from the sucked sample by the sample preparation section 22. In Step S3, components of the analysis target are detected from the detection sample by the detection section 23. In Step S4, measurement data is transmitted from the first measurement unit 2 to the control device 5. Then, in Step S5, the components of the analysis target are analyzed by the control unit 51 on the basis of the measurement result transmitted from the first measurement unit 2. The analysis of the sample is completed by Step S5, and the operation is completed.

Figure 12:
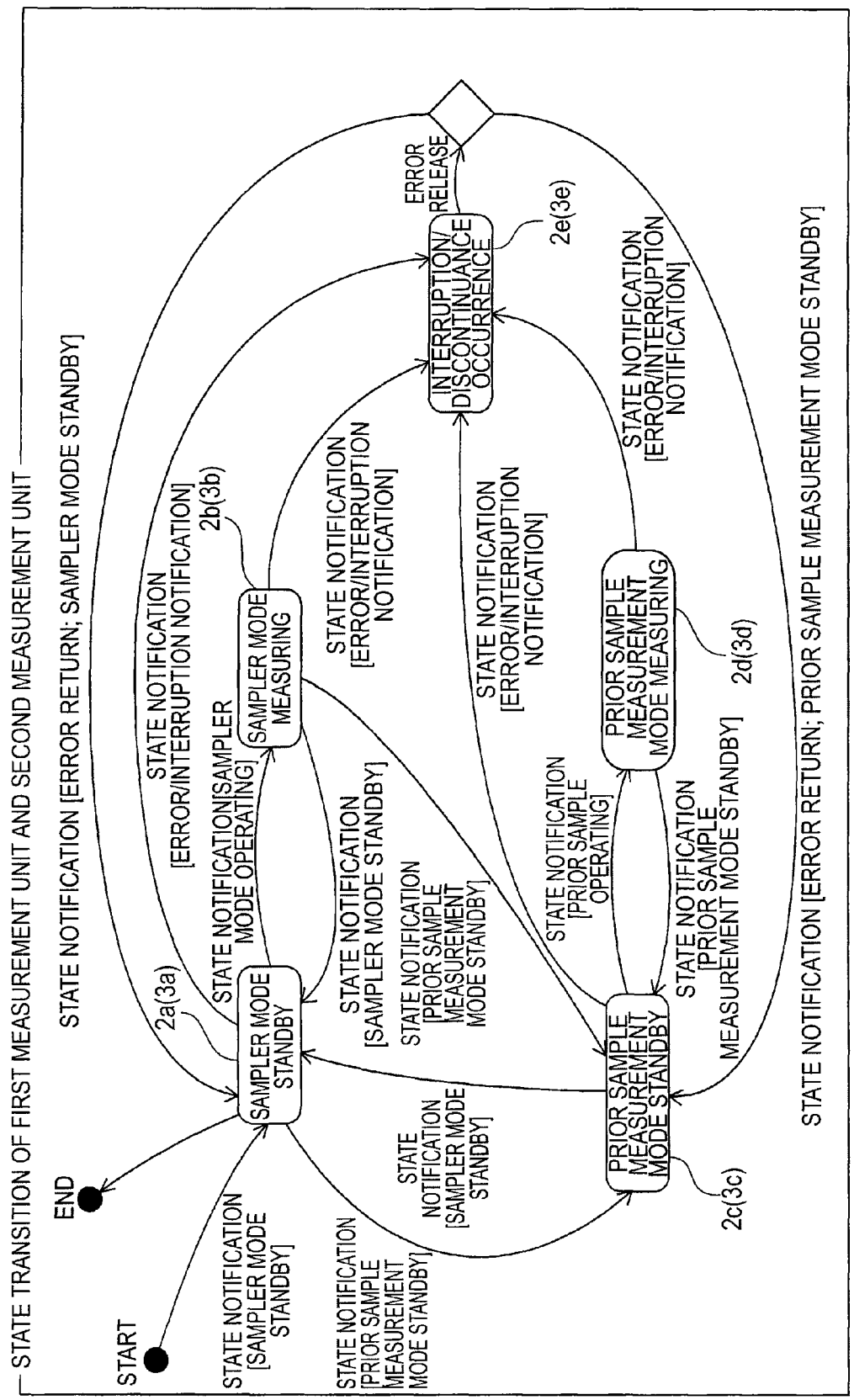
FIG. 12 is a state transition diagram for explaining state transition of a first measurement unit and a second measurement unit of the blood analyzer according to the embodiment shown in FIG. 1.

FIG. 12 is a state transition diagram for explaining state transition of the first measurement unit and the second measurement unit of the blood analyzer according to the embodiment shown in FIG. 1. Next, the state transition of the first measurement unit 2 and the second measurement unit 3 of the blood analyzer 1 according to the embodiment will be described with reference to FIG. 12. In the first measurement unit 2 and the second measurement unit 3, each state transition is the same. Accordingly, hereinafter, the state transition of the first measurement unit 2 will be described as a representative example.

The state of the first measurement unit 2 is transited from a non-operating state (start) to a sampler mode standby state 2a by powering on. In the sampler mode standby state 2a, when sampler measurement start is instructed by a user, the first measurement unit 2 is transited to a sampler mode measuring state 2b. In the sampler mode measuring state 2b, the measurement processing operations shown in FIG. 11 are performed by the first measurement unit 2. In the sampler mode measuring state 2b, when the measurement of the sample is completed, the first measurement unit 2 is returned to the sampler mode standby state 2a. In the sampler mode standby state 2a, when the power is turned off, the first measurement unit 2 is transited to the non-operating state (end).

When the sample set section open and close button 26 is pressed down by a user in the sampler mode standby state 2a and the sampler mode measuring state 2b, the first measurement unit 2 is transited to a prior sample measurement mode standby state 2c. When the first measurement unit 2 is transited to the prior sample measurement mode standby state 2c, the transportation of the sample to the first measurement unit 2 is reserved. That is, in this case, the sample transportation device 4 does not transport the samples to the providing position 43a of the first measurement unit 2, but transports the samples only to the providing position 43b of the second measurement unit 3. When both of the first measurement unit 2 and the second measurement unit 3 are transited to the prior sample measurement mode standby state 2c, the transportation of the samples are reserved to both of the providing positions 43a and 43b.

In the prior sample measurement mode standby state 2c, when the prior sample measurement start button 27 is pressed down, the first measurement unit 2 is transited to the prior sample measurement mode measuring state 2d. When the measurement of the prior sample is completed, the first measurement unit 2 is returned to the prior sample measurement mode standby state 2c. When the measurement of all prior samples are completed, the first measurement unit 2 is transited to the sampler mode standby state 2a by pressing down the sample set section open and close button 26 by a user.

In each state of the sampler mode standby state 2a, the sampler mode measuring state 2b, the prior sample measurement mode standby state 2c, and the prior sample measurement mode measuring state 2d, when an error occurs, the first measurement unit 2 is transited to an interruption/discontinuance occurrence state 2e. When the error is removed, the first measurement unit 2 is returned to the mode standby state of each state. Specifically, when the error occurring in the sampler mode standby state 2a and the sampler mode measuring state 2b is removed, the first measurement unit 2 is returned to the sampler mode standby state 2a. When the error occurring in the prior sample measurement mode standby state 2c and the prior sample measurement mode measuring state 2d is removed, the first measurement unit 2 is returned to the prior sample measurement mode standby state 2c.

When the state of the first measurement unit 2 is transited, a state notification for notifying that the first measurement unit 2 is transited to any state is transmitted from the first measurement unit 2 to the control device 5. Specifically, when the first measurement unit 2 is transited from the sampler mode measuring state 2b, the prior sample measurement mode standby state 2c, and the interruption/discontinuance occurrence state 2e to the sampler mode standby state 2a, a state notification for notifying that the first measurement unit 2 is transited to the sampler mode standby state 2a is transmitted from the first measurement unit 2 to the control device 5. When the first measurement unit 2 is transited to the sampler mode measuring state 2b, the prior sample measurement mode standby state 2c, the prior sample measurement mode measuring state 2d, and the interruption/discontinuance occurrence state 2e, the state notification is transmitted to the control device 5 similarly with the case of the transition to the sampler mode standby state 2a. In addition, when the first measurement unit 2 is returned from the interruption/discontinuance occurrence state 2e to each state, a state notification for notifying that the first measurement unit 2 is transited to any state is transmitted from the first measurement unit 2 to the control device 5, and a notification for notifying that the error is removed is notified together.

Figure 13:
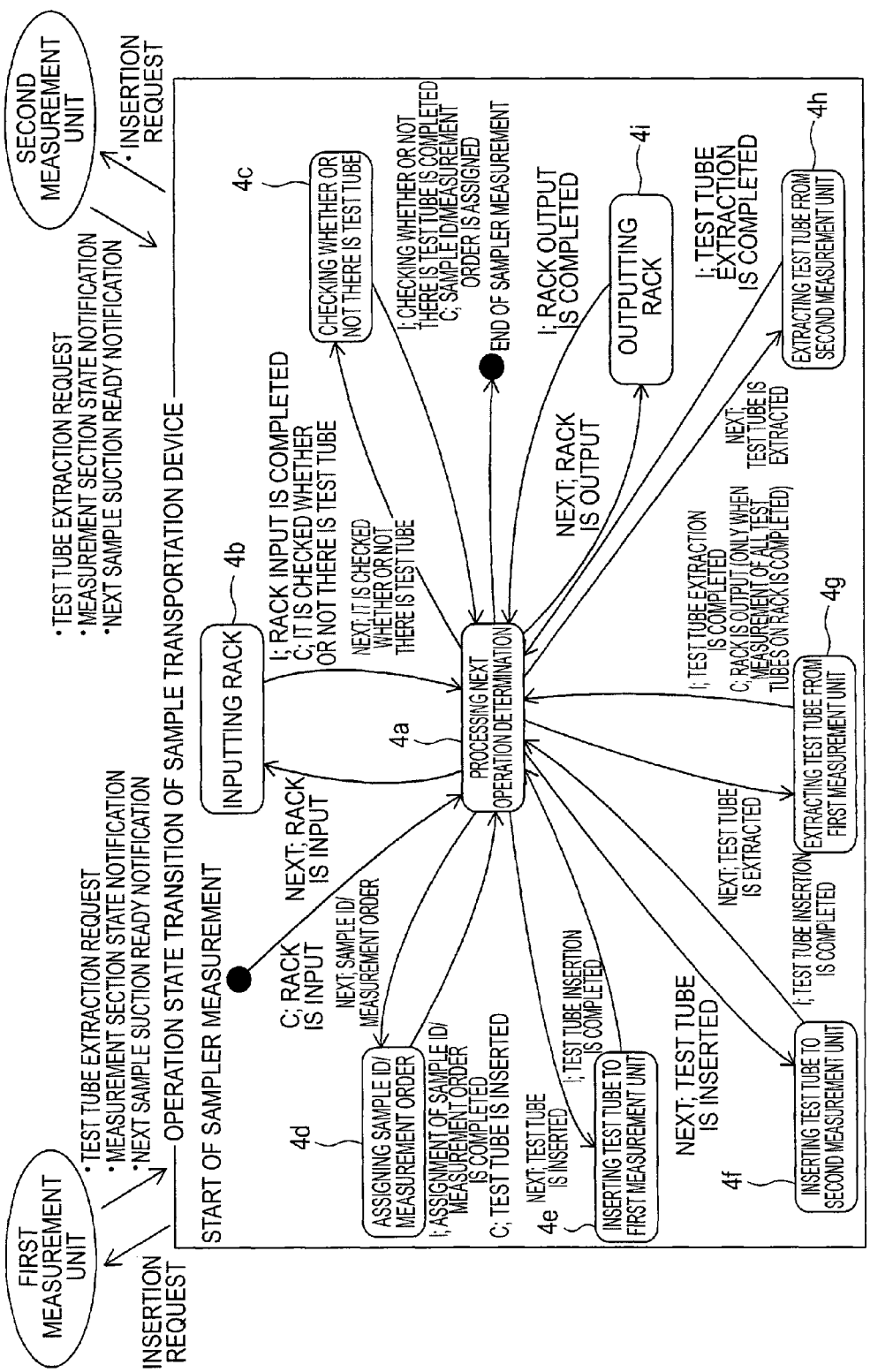
FIG. 13 is a state transition diagram for explaining state transition of a sample transportation device of the blood analyzer according to the embodiment shown in FIG. 1.
Figure 14:
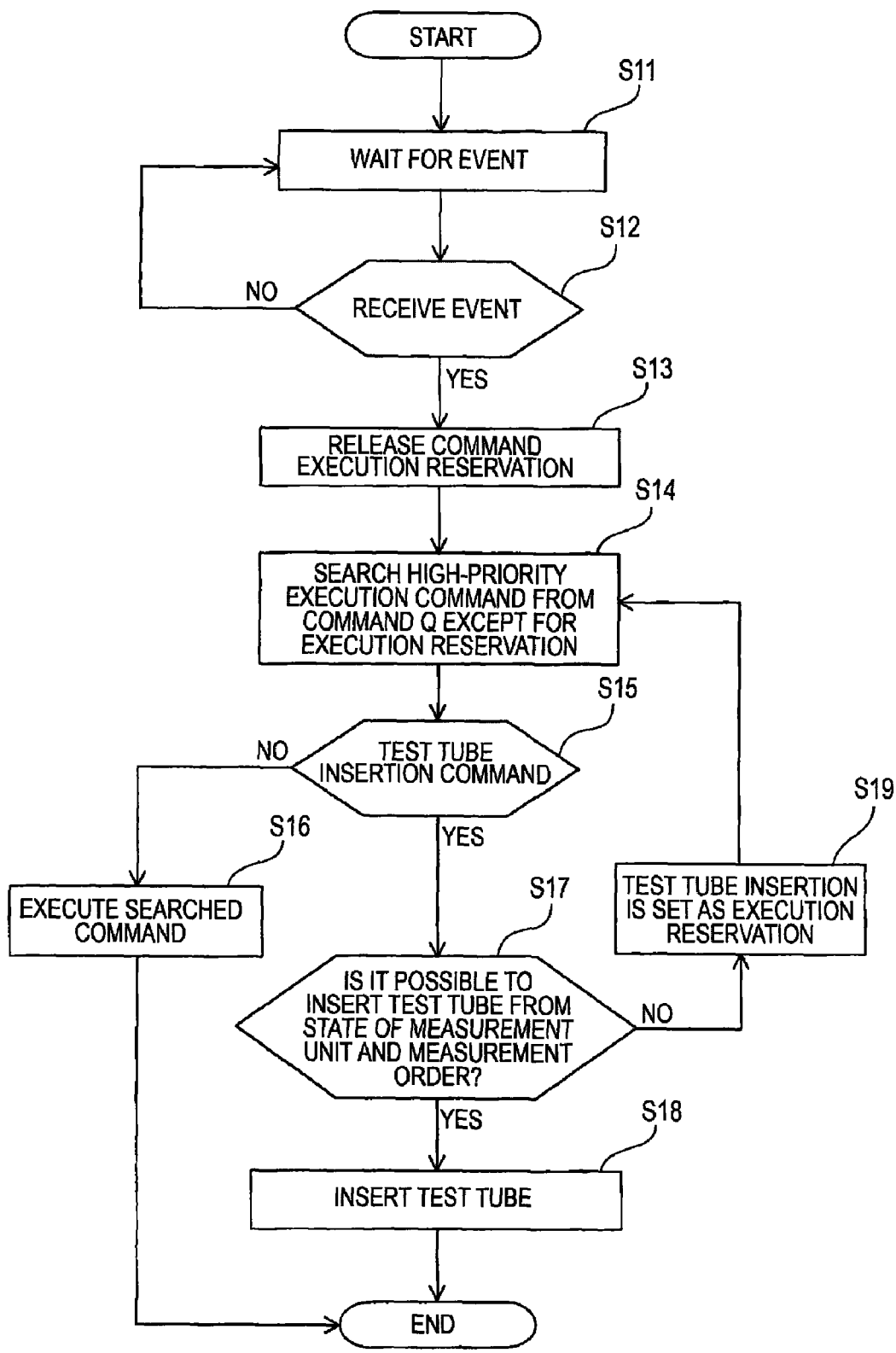
FIG. 14 is a flowchart for explaining a process of determining the next operation of the sample transportation device of the blood analyzer according to the embodiment shown in FIG. 1.

FIG. 13 is a state transition diagram for explaining state transition of the sample transportation device of the blood analyzer according to the embodiment shown in FIG. 1. FIG. 14 is a flowchart for explaining a process of determining the next operation of the sample transportation device of the blood analyzer according to the embodiment shown in FIG. 1. FIG. 15 and FIG. 16 are diagrams for explaining a detailed configuration of the blood analyzer according to the embodiment shown in FIG. 1. First, the state transition of the sample transportation device 4 of the blood analyzer 1 according to the embodiment will be described with reference to FIG. 13.

When a user instructs sampler measurement start, the state of the sample transportation device 4 becomes a next operation determination processing state 4a. This state is a waiting state for the sample transportation device 4 to execute operations registered in a queue for registering commands. In the embodiment, the queue is a data structure in which operation instructions to the sample transportation device 4 are registered, and the sample transportation device 4 is controlled by the CPU 51a of the control device 5 to execute the operations registered in the queue. The queue is stored in the RAM 51c or the hard disk 51d of the control device 5.

The process of determining the next operation performed by the sample transportation device 4 when the sample transportation device 4 of the blood analyzer 1 according to the embodiment is in the next operation determination processing state 4a will be described with reference to FIG. 14 to FIG. 16.

In Step S11 shown in FIG. 14, a notification of an event is waited by the CPU 51a. The notification of the event is notifications of 11 kinds of events shown in FIG. 15, and includes a notification for notifying that a predetermined operation is completed, a state notification for notifying a state of the measurement unit, and the like. Specifically, when the rack 101 is input from the before-analysis rack holding section 41 of the sample transportation device 4 onto the rack transportation section 43, a rack input completion notification is transmitted from the sample transportation device 4 to the control device 5. When the rack 101 on the rack transportation section 43 is output to the after-analysis rack holding section 42 by the rack output section 46, a rack output completion notification is transmitted from the sample transportation device 4 to the control device 5. When it is sensed whether or not there is the sample container 100 by the presence sensing sensor 45 of the sample transportation device 4, a test tube presence check completion notification is transmitted. When the barcode 100a of the sample container 100 is read by the barcode reading section 44 and a measurement order is assigned, a sample ID/measurement order assignment completion notification is transmitted.

A test tube insertion completion notification to first measurement unit, a test tube insertion completion notification to second measurement unit, a test tube extraction completion notification from first measurement unit, and a test tube extraction completion notification from second measurement unit are transmitted from the first measurement unit 2 and the second measurement unit 3 to the control device 5, when each operation in the first measurement unit 2 and the second measurement unit 3 is completed. In addition to state notifications of the first measurement unit 2 and the second measurement unit 3, a test tube extraction request notification for notifying that the sample container 100 is ready to be extracted from the first measurement unit 2 and the second measurement unit 3 and a next sample suction ready notification for notifying that a next new sample is ready to be sucked are transmitted from the first measurement unit 2 and the second measurement unit 3 to the control device 5.

In Step S12, it is determined whether or not any one of event notifications of the 11 kinds of event notifications is received by the CPU 51a, and the event notification waiting state continues until any one of event notifications is received. When any one of event notifications is received, the execution reservation of the operation set in the reservation state not to be performed among the operations registered in the queue is released by the CPU 51a, in Step S13.

The execution reservation will be described hereinafter. In the embodiment, as shown in FIG. 16, the operations registered in the queue are provided with priorities, and a high-priority operation is selected from the operations registered in the queue at the time of performing the operation by the CPU 51a. The sample transportation device 4 is controlled to perform the selected operation by the CPU 51a. However, there may be a case where two operations of "test tube insertion to first measurement unit" and "test tube insertion to second measurement unit" cannot be instantly performed, for example, a case where there is the other sample, which is being measured, in the first measurement unit 2 and the second measurement unit 3, and the next new sample cannot be inserted. In such a case, the execution of the operations of "test tube insertion to first measurement unit" and "test tube insertion to second measurement unit" is set as a reservation state by the CPU 51a, so that the operations of "test tube insertion to first measurement unit" and "test tube insertion to second measurement unit" are skipped and a subsequent high-priority operation is first performed. Accordingly, in the blood analyzer 1 according to the embodiment, even when the operations of "test tube insertion to first measurement unit" and "test tube insertion to second measurement unit" cannot be performed, the other operation than "test tube insertion to first measurement unit" and "test tube insertion to second measurement unit" is first performed. Therefore, it is possible to promptly perform the process of the samples.

In Step S14, the highest-priority operation is searched from the operations registered in the queue in the present state by the CPU 51a. In Step S15, it is determined whether the searched highest-priority operation is any one of "test tube insertion to first measurement unit" or "test tube insertion to second measurement unit". When the operation is not any one of "test tube insertion to first measurement unit" and "test tube insertion to second measurement unit", the searched highest-priority operation is performed in Step S16. At this time, when the rack output operation is performed, the rack output section 46 is controlled to output the rack 101 on the rack transportation section 43 to the after-analysis rack holding section 42 by the CPU 51a. When the rack input operation is performed, the rack input section 411 is controlled to input the rack 101 of the before-analysis rack holding section 41 onto the rack transportation section 43 by the CPU 51a. When the test tube extraction operation from the first measurement unit or the test tube extraction operation from the second measurement unit is performed, the rack transportation section 43 is controlled to transport the rack 101 by the CPU 51a, so that the container accommodating section 101b of the extracted sample container 100 corresponds to any one of the providing position 43a of the first measurement unit 2 or the providing position 43b of the second measurement unit 3. When the test tube presence check operation is performed, the rack transportation section 43 is controlled to transport the rack 101 by the CPU 51a, so that the unchecked sample container 100 accommodated in the rack 101 reaches the sample presence check position 43c. When the sample ID/measurement order assignment operation is performed, the rack transportation section 43 is controlled to transport the rack 101, so that the sample container 100 accommodated in the rack 101 and to which a measurement order is not yet assigned reaches the reading position 43d. Then, the operation is completed.

On the other hand, when the operation is any one operation of "test tube insertion to first measurement unit" or "test tube insertion to second measurement unit", it is determined whether or not the corresponding operation of "test tube insertion to first measurement unit" or "test tube insertion to second measurement unit" can be performed by the CPU 51a on the basis of the measurement order and the state of the first measurement unit 2 and the second measurement unit 3 in Step S17.

In the embodiment, the CPU 51a determines whether or not the measurement unit corresponding to the first measurement unit 2 or the second measurement unit 3 is in a state capable of inserting the test tube, on the basis of the state notifications transmitted from the measurement units, the test tube extraction request notification, and the next sample suction ready notification. Specifically, when the state notification indicating the prior sample measurement mode standby state 2c, the prior sample measurement mode measuring state 2d, or the interruption/discontinuance occurrence state 2e is transmitted from the first measurement unit 2, the CPU 51a determines that the test tube cannot be inserted to the first measurement unit 2. When the next sample suction ready notification is not transmitted from the first measurement unit 2, the CPU 51a determines that the first measurement unit 2 is not in the state capable of inserting the test tube. Determination for the second measurement unit 3 is performed in the same manner as the case of the first measurement unit 2. In the case capable of inserting the test tube, the corresponding operation of "test tube insertion to first measurement unit" or "test tube insertion to second measurement unit" is performed in Step S18. At this time, the rack transportation section 43 is controlled to transport the rack 101 by the CPU 51a, so that the container accommodating section 101b of the extracted sample container 100 reaches a position corresponding to any one of the providing position 43a of the first measurement unit 2 or the providing position 43b of the second measurement unit 3. Then, the operation is completed. In the case incapable of inserting the test tube, the execution of the corresponding operation of "test tube insertion to first measurement unit" or "test tube insertion to second measurement unit" is set as the reservation state by the CPU 51a in Step S19. Then, the process is transferred to Step S14, and the second-highest priority operation in the reservation state is searched from the operations registered in the queue. For example, when the operation of "test tube insertion to second measurement unit" is registered in the queue in the case where the operation of "test tube insertion to first measurement unit" is in the reservation state, "test tube insertion to second measurement unit" is searched.

As described above, the operation performed next time by the sample transportation device 4 is determined on the basis of the latest state of each of the first measurement unit 2 and the second measurement unit 3, immediately before the sampler transportation device 4 performs the next operation by CPU 51a. Accordingly, since the sample transportation device 4 can perform efficient transportation based on the latest state of each of the first measurement unit 2 and the second measurement unit 3, it is possible to promptly perform the process of the samples.

In the next operation determination processing state 4a shown in FIG. 13, when the next operation is performed by the above-described process of FIG. 14, the sample transportation device 4 is transited to states 4b to 4i corresponding to the operations. Specifically, the sample transportation device 4 may be transited to 9 kinds of states of a rack inputting state 4b, a test tube presence checking state 4c, a sample ID/measurement order assigning state 4d, a test tube inserting state 4e to first measurement unit, a test tube inserting state 4f to second measurement unit, a test tube extracting state 4g from first measurement unit, a test tube extracting state 4h from second measurement unit, and a rack outputting state 4i, in addition to the next operation determination processing state 4a.

In FIG. 13, the operations performed in the next operation state are shown, as "NEXT;". In FIG. 13, the events notified to the control device 5 at the time of being transited from each operation state to the next operation determination processing state 4a are shown, as "I;", and the operations registered in the queue are shown, as "C;". For example, when the sample transportation device 4 is in the rack inputting state 4b, the rack input operation shown as "NEXT;" is performed. When the sample transportation device 4 is transited from the rack inputting state 4b to the next operation determination processing state 4a, the event notification for notifying the rack input completion shown as "I;" is transmitted to the control device 5, and the test tube presence check operation shown as "C;" is registered in the queue by the CPU 51a. For the other event shown in FIG. 15, the notification is performed in the same manner as the rack input completion notification. In addition, for the other operation shown in FIG. 16, the registration to the queue is performed in the same manner as the test tube presence check operation. The two operations of "test tube extraction from first measurement unit" and "test tube extraction from second measurement unit" are registered in the queue on the basis of the test tube extraction request transmitted from the first measurement unit 2 and the second measurement unit 3.

In the case where the sample transportation device 4 is in the test tube inserting state 4e to first measurement unit, when the sample container 100 inserted to the first measurement unit 2 is transported to a predetermined position, the insertion request notification for notifying completion of transportation to a predetermined position is transmitted to the first measurement unit 2. On the basis of the notification, the CPU 51a can control the first measurement unit 2 so that the sample container 100 is gripped by the hand section 251. For the second measurement unit 3, the insertion request notification is transmitted in the same manner as the first measurement unit 2.

Figure 17:
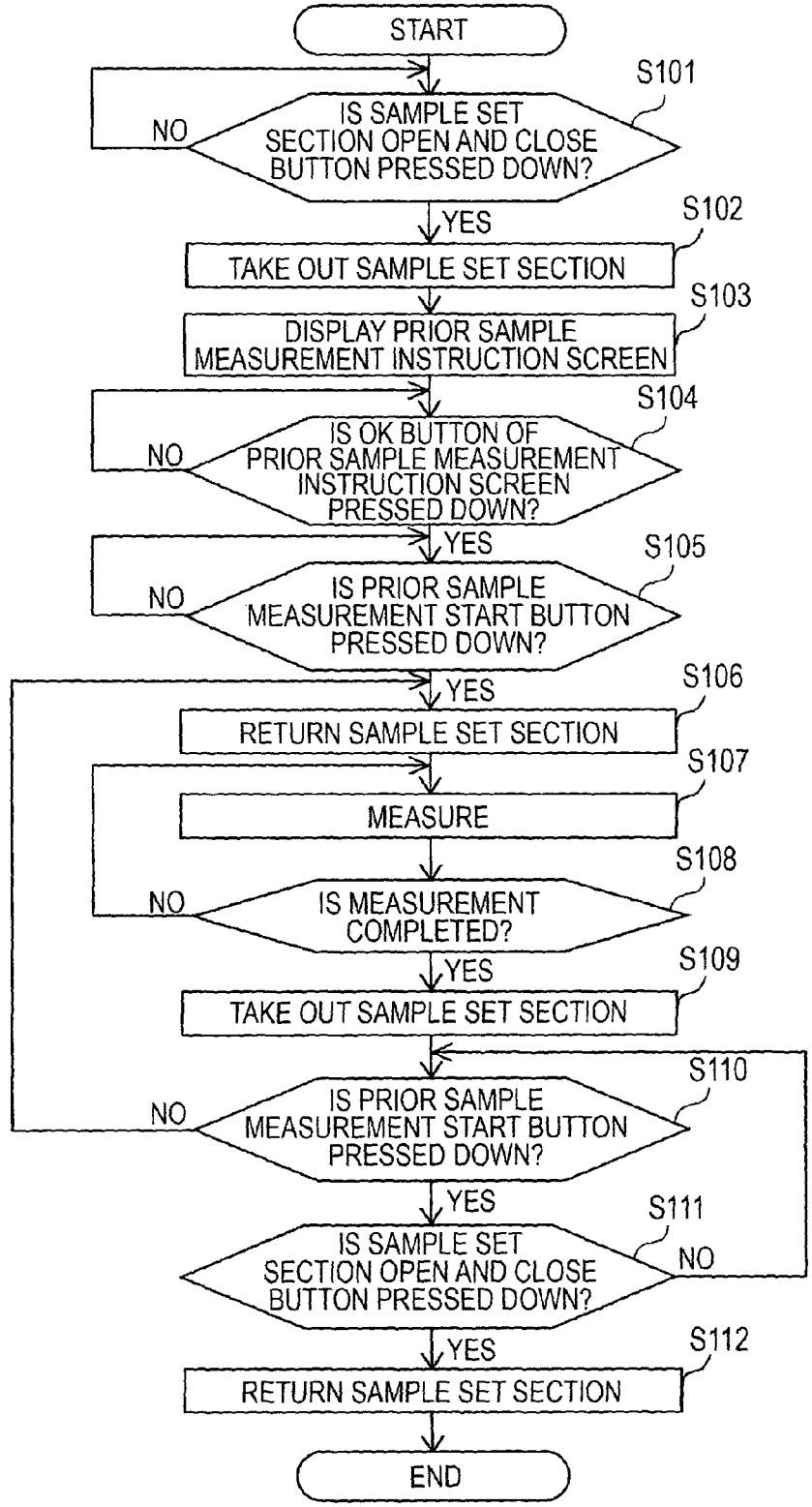
FIG. 17 is a flowchart for explaining an operation at the time of prior sample measurement of the blood analyzer according to the embodiment shown in FIG. 1.

FIG. 17 is a flowchart for explaining the operation at the time of prior sample measurement of the blood analyzer according to the embodiment shown in FIG. 1. Next, the operation at the time of prior sample measurement of the blood analyzer 1 according to the embodiment will be described with reference to FIG. 1, FIG. 2, FIG. 10, and FIG. 17. In the embodiment, the first measurement unit 2 and the second measurement unit 3 can measure prior samples independently from each other, and the operations at the time of prior sample measurement in the first measurement unit 2 and the second measurement unit 3 are the same. Accordingly, the operation at the time of prior sample measurement in the first measurement unit 2 will be described herein as a representative example.

First, in Step S101 shown in FIG. 17, it is determined whether or not the sample set section open and close button 26 (see FIG. 1 and FIG. 2) is pressed down by the CPU 51a, and the determination is repeated until the sample set section open and close button 26 is pressed down. When the sample set section open and close button 26 is pressed down, the sample set section 255a (see FIG. 2) protrudes out of the insertion hole 24 in Step S102. In Step S103, the prior sample measurement instruction screen 520 (see FIG. 10) is displayed on the display unit 52. In Step S104, after a user inputs a sample identification number or sets measurement items, it is determined whether or not the OK button 520a displayed on the prior sample measurement instruction screen 520 is pressed down by the CPU 51a. The determination is continued until the OK button 520a is pressed down. When the OK button 520a is pressed down, the user sets the sample container 100 accommodating the prior sample at the sample set section 255a in Step S105 and then it is determined whether or not the prior sample measurement start button 27 (see FIG. 1 and FIG. 2) is pressed down by the CPU 51a. When the prior sample measurement start button 27 is not pressed down, the determination is repeated. When the prior sample measurement start button 27 is pressed down, the sample set section 255a is returned from the insertion hole 24 to the inside of the first measurement unit 2 in Step S106. Accordingly, the prior sample is inserted into the first measurement unit 2.

In Step S107, the measurement of the prior sample is performed. In Step S108, it is determined whether or not the measurement is completed. The determination is repeated until the measurement completed. When the measurement is completed, the sample set section 255a comes out of the insertion hole 24 in Step S109. Accordingly, the sample container 100 of the measured prior sample is discharged out of the first measurement unit 2 so as to be extracted. Then, in Step S110, it is determined whether or not the prior sample measurement start button 27 is pressed down.

The user removes the sample container 100 of the measured prior sample from the sample set section 255a, and then sets the sample container 100 accommodating a next new prior sample at the sample set section 255a. The prior sample measurement start button 27 is pressed down, thereby continuously performing the measurement of the prior sample. When the user sets the sample container 100 accommodating the next new prior sample at the sample set section 255a and presses down the prior sample measurement start button 27, the operation is transferred to Step S106 and the measurement of the next prior sample is continuously performed. In this case, even when the user does not input the sample identification number or set the measurement items, continuous identification numbers are automatically assigned by the CPU 51a and the measurement is continued with the same items according to the once set measurement items.

When the prior sample measurement start button 27 is not pressed down, it is determined whether or not the sample set section open and close button 26 is pressed down by the CPU 51a in Step S111. The user can complete the measurement of the prior sample by pressing down the sample set section open and close button 26. When the sample set section open and close button 26 is not pressed down, the determination is repeated until any one of the prior sample measurement start button 27 and the sample set section open and close button 26 is pressed down. When the sample set section open and close button 26 is pressed down, the sample set section 255a is returned from the insertion hole 24 to the inside of the first measurement unit 2 in Step S112 and the measurement operation of the prior sample is completed.

In the embodiment, as described above, the CPU 51a is configured to determine whether or not the samples are transportable to the selected one measurement unit on the basis of the state notification of the first measurement unit 2 and the second measurement unit 3, to control the sample transportation device 4 to perform the sample transportation operation to the selected one measurement unit when it is determined that the samples are transportable to the selected one measurement unit, and to control the sample transportation device 4 to perform the other operation than the sample transportation operation when it is determined that the sample are not transportable to the selected one measurement unit. With such a configuration, when the samples are transportable, the samples are transported to the selected one measurement unit. When the samples are not transportable, the samples are not transported to the selected one measurement unit and the other operation than the sample transportation operation is performed. Accordingly, even when interruption cause of measurement occurs such as error and a measurement instruction of a prior sample in the selected one measurement unit, the process of the samples is not interrupted. Therefore, it is possible to promptly process the samples. In the blood analyzer 1, it is not determined by the CPU 51a whether or not the rack 101 accommodating a plurality of samples can be input onto the transportation path (transportation line), but it is determined by the CPU 51a whether or not the samples are transportable to the selected one measurement unit. Accordingly, even when the interruption cause of the measurement occurs in the selected one measurement unit after the rack 101 is input onto the transportation path (transportation line), it is possible to promptly cope with the occurrence of the interruption cause. As a result, it is possible to promptly process the samples.

In the embodiment, each of the state notification of the first measurement unit 2 and the state notification of the second measurement unit 3 includes the notification indicating the transition from the sampler mode (including the sampler mode standby states 2a and 3a, and the sampler mode measuring states 2b and 3b) of measuring the samples transported by the sample transportation device 4, to the prior sample measurement mode (including the prior sample measurement mode standby states 2c and 3c, and the prior sample measurement mode measuring states 2d and 3d) of measuring the prior sample prior to the samples transported by the sample transportation device 4, thereby determining whether or not the samples are transportable to the selected one measurement unit by the CPU 51a on the basis of the notification indicating that the first measurement unit 2 or the second measurement unit 3 is transited from the transportation sample measurement mode to the prior sample measurement mode. Accordingly, when the selected one measurement unit is in the prior sample measurement mode, the sample transportation device 4 does not perform the sample transportation operation to the selected one measurement unit, and can perform the other operation than the sample transportation operation. As a result, it is possible to process the samples without waiting for cancel of the prior sample measurement mode of the selected one measurement unit. Therefore, it is possible to suppress a decrease of a process speed of the samples.

In the embodiment, the state notification of the first measurement unit 2 includes the notification indicating that the first measurement unit 2 is transited to the interruption/discontinuance occurrence state 2e, and the state notification of the second measurement unit 3 includes the notification indicating that the second measurement unit 3 is transited to the interruption/discontinuance occurrence state 3e, thereby determining whether or not the samples are transportable to the selected one measurement unit by the CPU 51a on the basis of the notification indicating that the first measurement unit 2 or the second measurement unit 3 is transited to the interruption/discontinuance occurrence state 2e or 3e. Accordingly, when the selected one measurement unit is transited to the interruption/discontinuance occurrence state 2e or 3e, the sample transportation device 4 does not perform the sample transportation operation to the selected one measurement unit, and can perform the other operation than the sample transportation operation. As a result, it is possible to process the samples without waiting until the selected one measurement unit is transited to the sampler mode standby state 2a or 3a or is transited to the prior sample measurement mode standby state 2c or 3c. Therefore, it is possible to suppress a decrease of a process speed of the samples.

All the above-described embodiments are only examples, and it should be considered that they are not restrictive examples. The scope of the invention is not limited to the description of the embodiments, but is limited only by Claims. In addition, the scope of the invention includes all modifications within the means and scope equivalent to Claims.

For example, in the embodiment, the blood analyzer has been described as an example of an analyzer, but the invention is not limited thereto. The invention may be applied to the other analyzer as long as it is an analyzer provided with a plurality of measurement units.

In the embodiment, the blood analyzer is provided with two measurement units of the first measurement unit and the second measurement unit by way of example, but the invention is not limited thereto. The blood analyzer may be provided with three or more measurement units.

In the embodiment, the sample container is taken out of the rack and is input into the measurement unit by way of example, but the invention is not limited thereto. The samples may be sucked from the sample container accommodated in the rack by the sample suction section, the sample container may not be input into the measurement unit, and only the sample may be input.

In the embodiment, the control device is provided with one control unit by way of example, but the invention is not limited thereto. The first measurement unit and the second measurement unit may be provided with different control units, respectively. Theses control units may be mounted on the first measurement unit and the second measurement units, respectively.

Figure 18:
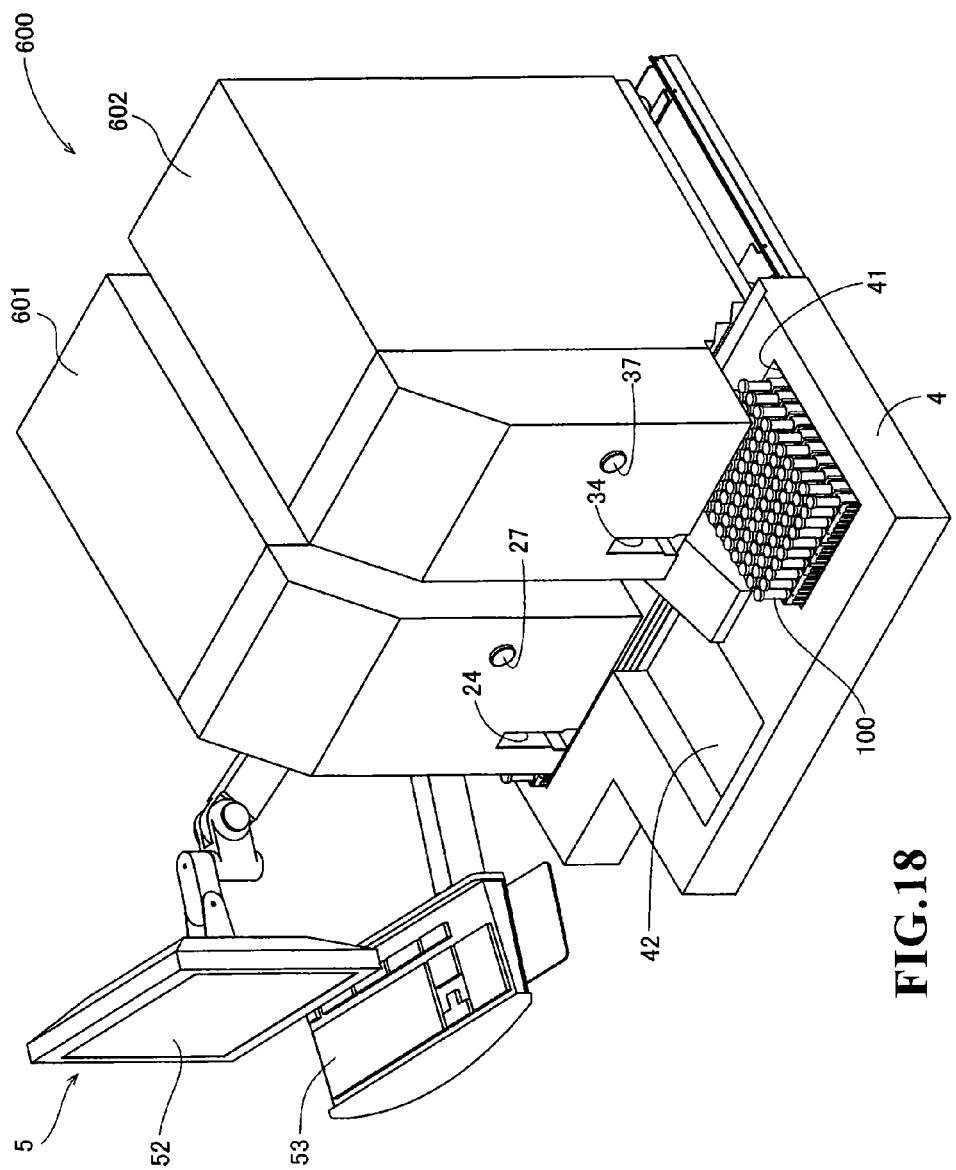
FIG. 18 is a diagram for explaining a modified example of the blood analyzer according to the embodiment of the invention.

In the embodiment, the first measurement unit and the second measurement unit are accommodated in the independent different housings, respectively, by way of example (see FIG. 1 and FIG. 2), but the invention is not limited thereto. As shown in FIG. 18, the first measurement unit and the second measurement unit may be accommodated together in one housing 7.

In the embodiment, the first measurement unit and the second measurement unit are substantially the same type of measurement units by way of example, but the invention is not limited thereto. The first measurement unit and the second measurement unit may be different types of measurement units.

What is claimed is:

1. An analyzer comprising:
    a first measurement unit;
    a second measurement unit; and
    a transportation device for transporting samples to at least one measurement unit selected from the first measurement unit and the second measurement unit, the transportation device comprising:
        a first rack holding section configured to receive one or more racks of sample containers;
        a second rack holding section configured to receive one or more racks of sample containers on which measurements for the sample containers are completed;
        a transportation path arranged between the first and second rack holding sections, the first and second measurement units arranged along the transportation path;
        a transporting member movable along the transportation path in a first direction from the first rack holding section to the second rack holding section and in the opposite direction of the first direction, the transporting member being configured to hold a rack of sample containers and to transport the sample container of the rack to one of the first and second measurement units; and
        a transportation controller configured to control the transportation device, the transportation controller performing a transporting operation for each of sample containers of a rack, the transporting operation comprising:
            receiving from each of the first and second measurement units state information of a state of the respective measurement units;
            selecting, as a destination of a sample container to be transported, the first measurement unit when received state information indicates that the first measurement unit is ready to perform a measurement on a sample transported via the transportation path; and
            controlling the transportation device to actuate the transporting member so as to transport the sample container to the first measurement unit.

2. The analyzer of claim 1, wherein the transportation controller selects as the destination the second measurement unit when received state information indicates that the first measurement unit is not ready but the second unit is ready and controls the transportation device to actuate the transporting member so as to transport the sample container to the second measurement unit.

3. The analyzer of claim 2, wherein the transportation controller suspends the transportation when received state information indicates that both of the first and second measurement units are not ready.

4. The analyzer of claim 1, wherein the transportation controller alternatively selects as the destination the second measurement unit when receiving a state information indicating that the first measurement unit is not ready after selecting the destination.

5. The analyzer of claim 4, wherein when an error has occurred in the first measurement unit, the transportation controller receives a state information indicating that the first measurement unit is not ready.

6. The analyzer of claim 4, wherein when an operation mode of the first measurement unit is altered to a prior mode for measuring a sample to be measured in higher priority than other sample, the transportation controller receives a state information indicating that the first measurement unit is not ready.

7. The analyzer of claim 1, wherein the first and second measurement units are configured to perform measurements on same measurement item.

8. The analyzer of claim 1, wherein the sample container is capped with a cap, and the first and second measurement units comprise a needle for penetrating the cap and aspirating the content of the sample container.

9. The analyzer of claim 1, wherein the sample in the sample container comprises blood.

10. The analyzer of claim 1, wherein the transportation device further comprises a rack feeder for feeding out a rack placed at a feed out position on the transportation path to the second rack holding section, and the transportation controller controls the transportation device to:

transport by the transporting member a rack to the feed out position when measurements of sample containers on the rack are completed; and feed out by the rack feeder the rack to the second rack holding section.

* * * * *